United States Patent
Santiago

(10) Patent No.: US 12,431,226 B2
(45) Date of Patent: Sep. 30, 2025

(54) INTELLIGENT GENERATION OF PERSONALIZED CQL ARTIFACTS

(71) Applicant: SAFI Clinical Informatics Group, LLC, Kingwood, TX (US)

(72) Inventor: Fredric A. Santiago, Kingwood, TX (US)

(73) Assignee: SAFI Clinical Informatics Group, LLC, Kingwood, TX (US)

( * ) Notice: Subject to any disclaimer, the term of this patent is extended or adjusted under 35 U.S.C. 154(b) by 0 days.

(21) Appl. No.: 18/673,079

(22) Filed: May 23, 2024

(65) Prior Publication Data

US 2025/0046407 A1 Feb. 6, 2025

Related U.S. Application Data

(60) Provisional application No. 63/530,045, filed on Jul. 31, 2023.

(51) Int. Cl.
G16H 10/60 (2018.01)
G16H 50/50 (2018.01)

(52) U.S. Cl.
CPC .............. G16H 10/60 (2018.01); G16H 50/50 (2018.01)

(58) Field of Classification Search
None
See application file for complete search history.

(56) References Cited

U.S. PATENT DOCUMENTS

| | | | | |
|---|---|---|---|---|
| 12,020,814 B1 * | 6/2024 | McNair | | G16H 50/70 |
| 2015/0120321 A1 * | 4/2015 | David | | G16H 10/60 |
| | | | | 705/2 |
| 2016/0378950 A1 * | 12/2016 | Reiner | | G16H 70/40 |
| | | | | 705/2 |
| 2018/0121622 A1 * | 5/2018 | Armstrong | | G06N 5/01 |
| 2018/0196921 A1 | 7/2018 | Devarakonda et al. | | |
| 2018/0315495 A1 * | 11/2018 | Chekroud | | G16H 20/00 |

(Continued)

FOREIGN PATENT DOCUMENTS

| | | | |
|---|---|---|---|
| AU | 2021200650 A1 * | 9/2021 | |
| WO | 2025029357 | 2/2025 | |

OTHER PUBLICATIONS

Xi Yang et al., A large language model for electronic heath records, NPJ Digital Medicine 5:194 (2022) (Year: 2022).*

(Continued)

*Primary Examiner* — Jonathon A. Szumny
*Assistant Examiner* — Nicholas Akogyeram, II
(74) *Attorney, Agent, or Firm* — Schwegman Lundberg & Woessner, P.A.

(57) ABSTRACT

Described is a system for receiving a disease specific treatment algorithm corresponding to a disease of a patient from a first Electronic Health Record (EHR) system, processing data corresponding to the disease specific treatment algorithm using a Large Language Model (LLM), receiving one or more CQL models from the LLM based on the processing of the data corresponding to the disease specific treatment algorithm, receiving an update to a patient record of the patient from the first EHR system, based on the update to the patient record and the one or more CQL models, triggering a Clinical Decision Support (CDS) hook to generate an alert, and causing transmission of the alert for a medical practitioner associated with the first EHR system.

20 Claims, 10 Drawing Sheets

(56) References Cited

U.S. PATENT DOCUMENTS

| | | | |
|---|---|---|---|
| 2021/0200766 A1* | 7/2021 | Erdmann | G06F 16/248 |
| 2022/0084662 A1* | 3/2022 | Das | A61B 5/02055 |
| 2023/0197278 A1* | 6/2023 | Griffin | G16H 50/30 |
| | | | 705/2 |
| 2023/0335258 A1* | 10/2023 | Sinha | G16H 20/60 |

OTHER PUBLICATIONS

"International Application Serial No. PCT/US2024/030850, International Search Report mailed Sep. 6, 2024", 2 pgs.
"International Application Serial No. PCT/US2024/030850, Written Opinion mailed Sep. 6, 2024", 5 pgs.
Yang, X., et al., "A Large Language Model for Electronic Health Record", npj Digital Medicine, vol. 5, Article 194, [Online]. Retrieved from the Internet: <http://doi.org/101038/s41746-022-00742-2>, (Dec. 26, 2022), 1-9.

* cited by examiner

INTELLIGENT GENERATION OF PERSONALIZED CQL ARTIFACTS

CLAIM OF PRIORITY

This application claims the benefit of priority under 35 U.S.C. § 119(e) to U.S. Provisional Patent Application No. 63/530,045, filed on Jul. 31, 2023, which is incorporated by reference herein in its entirety.

TECHNICAL FIELD

The present disclosure relates generally to clinical logical models, and more specifically to apply natural language processing for clinical logical models.

BACKGROUND

Fast Healthcare Interoperability Resources (FHIR, pronounced "fire") is an innovative, next-generation standards framework developed by Health Level Seven International (HL7), a not-for-profit standards developing organization that's dedicated to providing a comprehensive framework and related standards for the exchange, integration, sharing, and retrieval of electronic health information.

FHIR leverages contemporary web-based suite of API technology for user interface integration. This FHIR interoperability framework is designed to simplify implementation without sacrificing information integrity, being capable of modeling complex healthcare relationships and processes.

BRIEF DESCRIPTION OF THE SEVERAL VIEWS OF THE DRAWINGS

In the drawings, which are not necessarily drawn to scale, like numerals may describe similar components in different views. To identify the discussion of any particular element or act more easily, the most significant digit or digits in a reference number refer to the figure number in which that element is first introduced. Some non-limiting examples are illustrated in the figures of the accompanying drawings in which.

DETAILED DESCRIPTION

Figure 1:
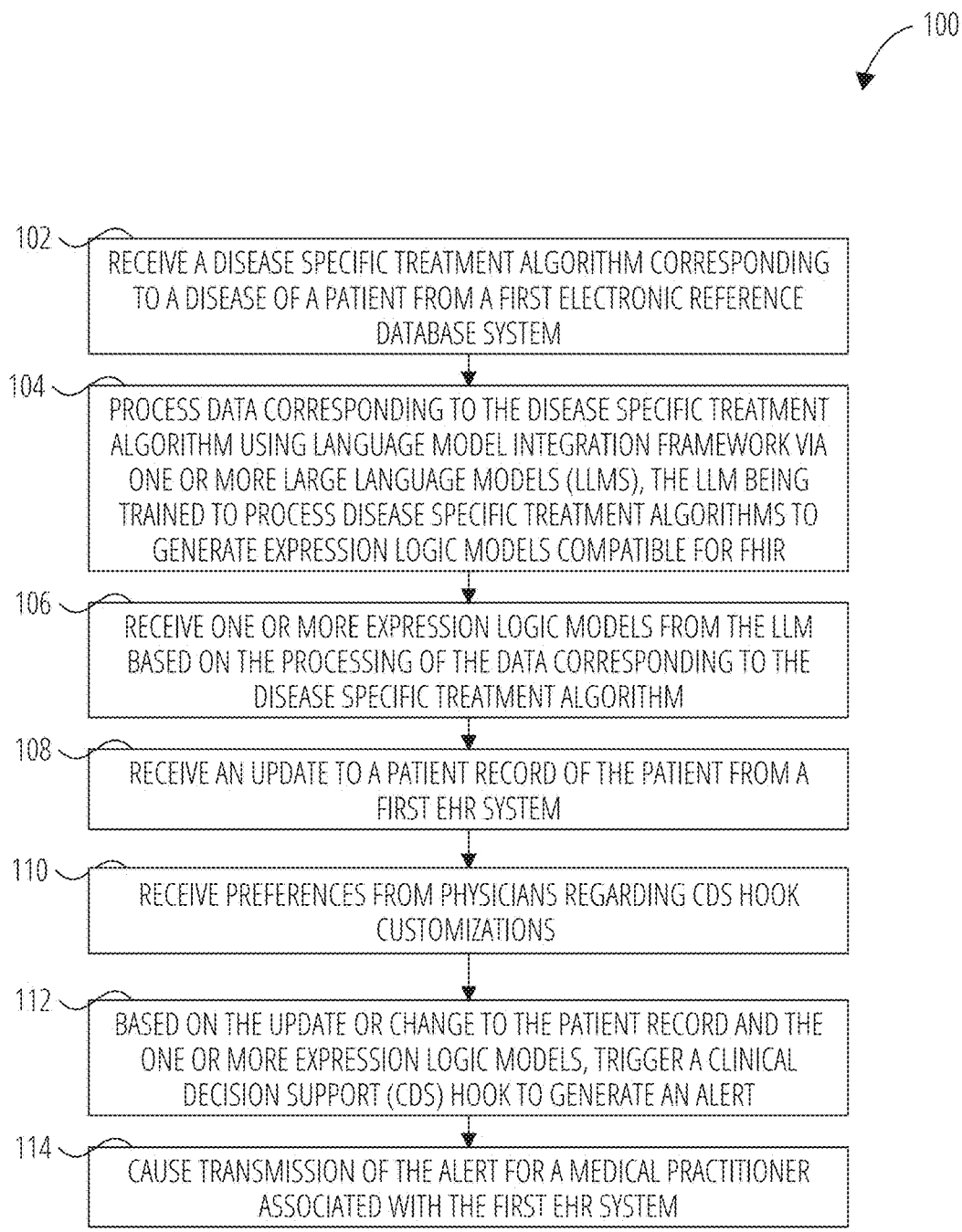
FIG. 1 illustrates an example method for applying a disease specific treatment algorithm to generate alerts for medical practitioners, according to some examples.

As noted above, FHIR is a standards framework for the exchange, integration, sharing, and retrieval of electronic health information. FHIR is built upon the concept of "Resources," which are modular components of interoperable health data. These Resources can represent clinical data like patients, practitioners, medications, and observations, or non-clinical data like devices, locations, and organizations. FHIR uses web-based technologies such as HTTP, HTML, CSS, JSON, XML, and RDF for data representation, which simplifies implementation and ensures greater interoperability between disparate health IT systems.

Clinical Decision Support (CDS) Hooks are a related specification that allows healthcare software to offer decision support within workflows at the point of care. CDS hooks act as triggers for specific workflow events within Electronic Health Records (EHRs) or other healthcare software. When such an event occurs (e.g., a medication is prescribed), the EHR makes a request to an external CDS Service, which then returns information directly relevant to that specific clinical scenario. This can include warnings about drug interactions, suggestions for diagnostic tests, or recommendations for disease management protocols.

Electronic Medical Records (EMRs) are digital versions of the traditional paper-based medical record for an individual. EMRs contain a patient's medical history, diagnoses, medications, treatment plans, immunization dates, allergies, radiology images, and laboratory and test results. They allow clinicians to track data over time, identify eligible patients for preventive screenings, monitor patients, and improve overall quality of care within an institution. EMRs are typically used by providers for diagnosis and treatment and are more of a patient history record within a single practice.

Although the examples described herein refer to a type of health record, such as EMRs, it is appreciated that the examples can be applied to other types of health records, such as EHRs, Electronic Reference Databases (ERDs), and/or the like. For example, the system applies EMR records that include a digital version of the traditional paper chart of a patient in a clinician's office, such as medical and treatment history of the patients in one practice. However, such examples can be applied to EHRs that can include information from all providers involved in a patient's care, including laboratories and specialists. In some examples, the disease specific treatment algorithm is received from one or more different databases, such as a collection of ERDs.

When these concepts are combined, FHIR allows different healthcare IT systems to communicate effectively, CDS Hooks can support clinical decisions by offering real-time, contextually appropriate clinical advice, and EMRs are the digital repositories of patient data.

In healthcare, CDS systems have been widely used to assist healthcare providers in making better decisions. These systems are based on algorithms, rules, and other tools to analyze patient data and provide relevant insights, alerts, and suggestions. However, these traditional systems have several issues.

Doctors and other healthcare providers receive numerous alerts causing alert fatigue due to the fact that many are irrelevant or redundant. The volume of alerts can be overwhelming, causing providers to potentially miss or ignore important notifications. This is exacerbated in the absence of context-specific alerting systems, leading to alerts that might not be appropriate for a particular patient's condition or circumstance.

Traditional CDS systems also lack the ability to adapt recommendations based on individual patient circumstances. The traditional systems often follow general rules, not taking into account unique aspects of a patient's condition, past medical history, or other personal factors. For instance, a general alert for a certain condition may not be applicable if the patient is on medications that negate side effects, or if the patient is of a certain type such that reactions to a medication are rare or inconsequential.

In traditional systems, knowledge representation often relied on complex, proprietary rule-based systems that were hard to understand, maintain, and share across different systems. CQL and FHIR standards were developed to address these issues, but they require specific programming knowledge, making them less accessible to doctors and other healthcare providers.

Moreover, traditional Artificial Intelligence (AI) systems produce biases or incorrect responses ('hallucinations'). Traditional AI systems are trained on vast amounts of data, such as information found on the general Internet, and if these data contain biases (such as racial or geographical biases), the AI can perpetuate these biases in its output. AI systems also lack a source of truth to check the validity of the training data, which can lead to incorrect or inappropriate recommendations.

Many traditional CDS systems are based on static rules, making it difficult to update them in response to new clinical evidence or changes in clinical guidelines. This means they can quickly become outdated.

The systems described herein aims to tackle these issues by leveraging AI to generate CQL models specific to disease and/or treatment profiles and adapt to be compatible with CDS Hooks based on each patient's unique circumstances. By doing so, the system reduces alert fatigue, provide personalized recommendations, and ensure up-to-date and unbiased decision support.

By using AI that takes disease-specific treatment algorithms as input, the system can generate more targeted, contextually appropriate alerts. The AI essentially filters out unnecessary notifications, focusing on only relevant, patient-specific alerts. This reduces the problem of alert fatigue, increasing the likelihood that doctors pay attention to each notification.

Moreover, the AI can receive as input a specific patient's record and apply the disease-specific CQL model to it. This allows for highly individualized recommendations. For example, if a patient has been provided with medications that negate certain side effects, the AI can consider this factor when generating alerts or recommendations (such as reducing or eliminating alerts pertaining to the side effects). This leads to more patient-centric custom tailored care.

The AI system auto-generates the CQL models that are applied to patient data, and when certain conditions are met, CDS hooks are triggered to generate cards (such as alerts) to be sent to doctors, circumventing the need for doctors to have programming knowledge. By adhering to standardized CQL and FHIR formats, the system ensures interoperability and seamless data exchange across different healthcare information systems.

The system trains the AI based on historical disease-specific treatment algorithms and patient diagnoses/treatment rather than indiscriminate internet data, which makes the AI far less prone to inherent biases or hallucinations. By training the AI specifically on real world medical data and procedures (or medical data/procedures that have been checked to make sense), the system can avoid many of the biases associated with an AI trained based on general internet data.

The AI system can continually process and learn from new patient records to update its disease-specific models and CDS hooks. Moreover, the AI system can continuously be trained or retrained based on updated guidelines. This ensures that the latest data and best practices inform decision-making processes for the AI. This adaptability keeps the system current, optimizing care over time.

The system uses CDS hooks to generate cards with actionable recommendations or alerts for doctors. This could include prescribing a different medication or dosage, changing a treatment, or sending reminders if certain drugs were not ordered or prescribed. This proactive approach aids physicians in making timely and informed decisions.

In some cases, the AI system generates CDS hooks for quality reporting. The CDS hooks generate reporting that meet requirements for EMR systems that are FHIR compatible. In some cases, the AI system generates CDS hooks for evidence and statistic reporting, which include the underlying data for the quality reporting.

In some cases, the AI system generates CDS hooks for order set production. For example, the AI system can request an order set production for a patient with hypertension, and the LLM generates an order set production for the physician. The order set production includes an expert opinion for a particular disease, prescriptions and corresponding dosages and schedules, diagnostic tests and procedures, care guidelines such as diet orders or activity orders, consultation orders such as for a specialist, clinical practice guidelines, patient specific information, discharge planning, precautions and contraindications related to treatment plans, outcome measures to track treatment and symptom scores, and/or the like.

In some cases, the AI system generates CDS hooks for defining a value for an element of an FHIR resource, such as ensuring data is up-to-date and relevant at the time it's used. In some cases, the AI system generates CDS hooks for defining a CQL library which includes expressing clinical knowledge that can be used in clinical decision support systems.

In some cases, the AI system generates CDS hooks for defining a model definition artifact, such as to use with expressions in FHIR to represent complex data structures or to define the structure of inputs and outputs for CQL libraries. In some cases, the AI system generates CDS hooks for defining an event condition action rule in FHIR, which can define actions to be taken when certain events occur under specific conditions.

In some cases, the AI system generates CDS hooks for defining a referral request activity which can then be used as part of a knowledge artifact. Such an artifact includes a structured document that defines a particular piece of clinical knowledge. In some cases, the AI system generates CDS hooks for defining a medication request activity to be used to define a medication request activity for use in a knowledge artifact.

In some cases, the AI system generates CDS hooks for defining an order set including a standardized group of clinical orders for a particular condition or procedure. In some cases, the AI system generates CDS hooks for defining a protocol which include detailed plans of medical treatment or research.

In some cases, the AI system generates CDS hooks for obtaining guidance from a decision support service which can involve sending patient data to the service and receiving recommended actions in return. In some cases, the AI system generates CDS hooks for defining a clinical quality measure used to assess the performance of individual clinicians, healthcare organizations, or health plans.

In some cases, the AI system generates CDS hooks for evaluating a measure, providing quantitative data on the quality of care being provided. In some cases, the AI system generates CDS hooks for applying an activity definition such as a medication or service request.

In some cases, the AI system generates CDS hooks for applying a plan definition such as for a specific patient or situation. In some cases, the AI system generates CDS hooks for representing quality of evidence and/or strength of recommendation, which can be used to rate the strength of the evidence supporting a particular artifact or the strength of a clinical recommendation.

The system trains the AI to handle variations in medical terminology by utilizing several strategies, including natural language processing (NLP), medical language processing, machine learning, and semantic understanding.

In summary, by using disease-specific algorithms and patient records to generate CQL models that trigger CDS hooks, the AI system can provide a more personalized, contextually appropriate, and bias-free decision support system that reduces alert fatigue and improves overall patient care.

When the effects in this disclosure are considered in aggregate, one or more of the methodologies described herein may improve known systems, providing additional functionality (such as, but not limited to, the functionality mentioned above), making them easier, faster, or more intuitive to operate, and/or obviating a need for certain efforts or resources that otherwise would be involved in a clinical logical model process. Computing resources used by one or more machines, databases, or networks may thus be more efficiently utilized or even reduced.

Applying Disease Specific Treatment Algorithms to Generate Alerts

FIG. 1 illustrates an example method 100 for applying a disease specific treatment algorithm to generate alerts for medical practitioners, according to some examples. Although the example method 100 depicts a particular sequence of operations, the sequence may be altered without departing from the scope of the present disclosure. For example, some of the operations depicted may be performed in parallel or in a different sequence that does not materially affect the function of the method 100. In other examples, different components of an example device or system that implements the method 100 may perform functions at substantially the same time or in a specific sequence.

FIG. 1 is described as being performed by certain systems or applying certain processes, such as a particular machine learning model or large language model (LLM), but the processes described herein can be performed by one or more other or the same machine learning models.

At operation 102, the AI system receives a disease specific treatment algorithm corresponding to a disease of a patient from a first electronic reference database system. The AI system interfaces with an electronic reference database system to access disease-specific treatment algorithms.

The disease specific treatment algorithm includes a structured set of guidelines or instructions for treating a specific disease, often in the form of a decision tree. The disease specific treatment algorithm is based on the patient's conditions, characteristics, and the current best practices in medical science. The disease specific treatment algorithm guides healthcare providers in choosing appropriate treatments, procedures, and medications.

In some cases, the disease specific treatment algorithm includes a structured set of guidelines or instructions for treating a specific disease that is general for the disease, whereby individual patient characteristics can be applied to determine best treatment, procedures, and medications for that particular patient with their own individual patient characteristics.

The EHR system includes data related to patients in the medical facility's care. In a healthcare context like a hospital or a clinic, the EHR system includes a computerized version of patient information, such as patient medical and treatment history provided by all doctors, specialists, and hospitals involved in the patient's care.

The AI system receives a specific set of instructions (the treatment algorithm) about how to treat a patient's disease from the digital health records maintained by the healthcare provider. This algorithm serves as a starting point for the AI to generate the CQL model.

Figure 2:
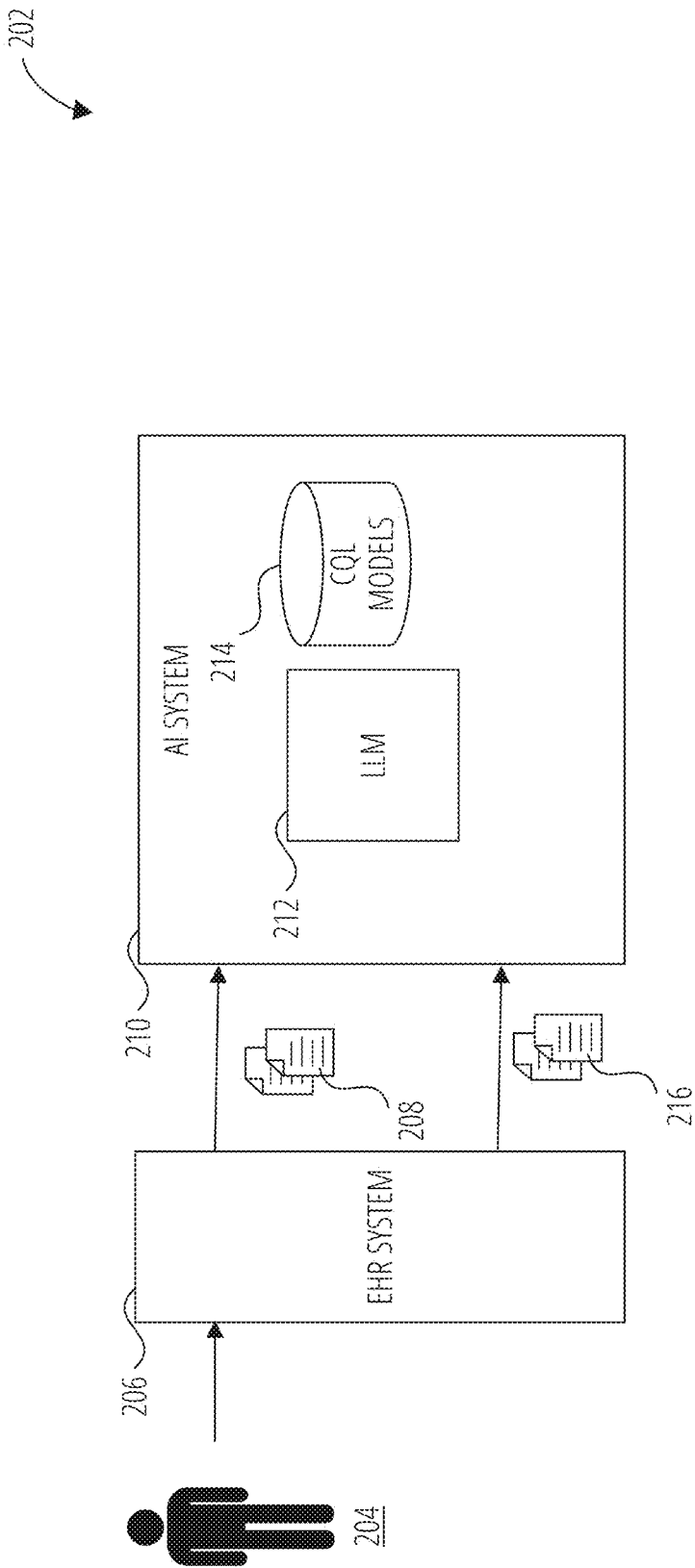
FIG. 2 illustrates an architecture for generating CQL models by applying disease specific treatment algorithms to an LLM, according to some examples.

FIG. 2 illustrates an architecture 202 for generating CQL models by applying disease specific treatment algorithms to an LLM, according to some examples. In the example of FIG. 2, a patient 204 enters into a medical facility for treatment of a disease. The patient 204 is diagnosed and a treatment plan is generated and stored by the EHR system 206. The EHR system sends a disease specific treatment algorithm 208 to the AI system 210.

In some cases, a disease-specific treatment algorithm for diabetes includes the following. The decision tree begins with an initial diagnosis, by determining if the patient has Type 1 or Type 2 diabetes based on medical history, physical examination, and blood tests (e.g., fasting glucose levels, HbA1c, etc.).

Regardless of the type of diabetes, data is collected of the patient regarding lifestyle and modifications to the lifestyle over time to keep the diabetes under control, such as whether the patient is eating healthy (carbohydrate counting, fat and calorie counting, eating at regular times, etc.), regularly exercising, determining if the patient is losing weight or is overweight/obese, and/or the like.

The decision tree determines for Type 1 diabetes, to start insulin therapy immediately. For Type 2 diabetes, if blood glucose levels remain uncontrolled despite lifestyle modifications, to consider starting oral medications such as Metformin.

The decision tree continues by checking whether the patient has uncontrolled glucose levels over time. For Type 1 diabetes, the decision tree recommends to adjust insulin dosage or type and to consider adding continuous glucose monitoring or insulin pump therapy if needed. For Type 2 diabetes, if blood glucose is not controlled with oral medication, the decision tree recommends considering adding another class of oral medication, a GLP-1 receptor agonist, or start insulin therapy.

The decision tree also includes adjustment of treatment based on continuous monitoring of certain physiological factors, such as blood glucose levels, HbA1c, kidney function, eye health, foot health, etc.

At operation 104, the AI system processes data corresponding to the disease specific treatment algorithm using a language model integration framework via one or more LLMs. The LLM is trained to process disease specific treatment algorithms to generate expression logic models (such as CQL models) compatible for FHIR. In some cases, the AI system applies a language model integration framework that connects one or more LLMs together. Moreover, the language model integration framework enables physicians to provide their own disease specific treatment algorithms and/or modifications to standard or predefined disease specific treatment algorithms, such as algorithms specific to their practice or patients. In some examples, one or more LLMs are used in order to receive one or more disease specific treatment algorithms, such as for a patient with multiple diseases. The language model integration framework is configured to apply prompt templates to determine the intent of the physicians based on a physician's prompt. As such, these language model integration frameworks better understand what physicians are asking for.

As shown in FIG. 2, the AI system 210 receives the disease specific treatment algorithm 208 and processes the disease specific treatment algorithm 208 using the LLM 212. The LLM 212 is trained to output the CQL models 214 stored in the CQL model database. The CQL models 214 are generated to be compatible with FHIR systems and CDS hooks.

Operation 104 involves applying AI, such as an LLM, to process the disease-specific treatment algorithm to generate an expression logic model where different conditions or characteristics of the patient lead to different actions or treatments.

Although examples described herein describe CQL models, it is appreciated that other expression models or logic apply. For example, the AI system applies an LLM trained to generate FHIR path models.

LLMs are machine learning models trained on a large corpus of text data and are trained to understand, generate, and transform human language in a meaningful and coherent way. When applied to the disease-specific treatment algorithm, the LLM "reads" and interprets the information contained in the disease specific treatment algorithm, including the actions and decisions it outlines. Importantly, it's been trained to understand this kind of medical information, using a combination of natural language processing, medical language processing, and FHIR treatment guidelines.

The LLM is trained using real life historical clinical documents and resulting model outcomes. The LLM is trained using CQL models, FHIR treatment guidelines, natural language processing, medical language processing, CDS hooks, and/or the like. In some cases, the training data for training the LLM does not include any data from the general Internet, but is a closed set of training data. In some cases, the training data for training the LLM only includes data from the general Internet for a particular portion of the training (such as only the natural language processing portion), but is a closed set of training data for other intents (such as medical language, FHIR treatment guidelines, and/or the like).

The AI system trains the LLM based on NLP training data, which enables the AI to understand, interpret, and generate human language in a valuable way. This training enables the AI to analyze unstructured text data in medical records, extracting key details and understanding the context. The AI is then able to identify important words or phrases that relate to medical conditions, treatments, and other relevant patient information.

The AI system trains the LLM based on medical language processing, which is a specialized form of NLP that's geared toward understanding medical terminology, which includes complex and often inconsistent terminologies used by different healthcare providers. Such training enables the LLM to comprehend various terms used to describe the same medical condition or treatment.

The AI system trains the LLM based on past data and make predictions or decisions without being explicitly programmed to do so. The AI system trains the LLM on a large dataset of FHIR treatment guidelines and CDS hooks, which include a variety of ways that medical conditions and treatments are described. After training, the LLM learns to associate different terminologies with the same medical conditions or treatments.

The AI system trains the LLM based on semantic understanding, which provides the LLM the ability to understand the meaning of words in context. This is vital in the medical field as the same word might have different meanings based on the context in which it is used. For example, "cold" could refer to a common viral infection, or it could refer to a low temperature. Semantic understanding enables the LLM to accurately interpret such words in the context of a patient's medical record.

Systems and methods described herein include training a machine learning network, such as training an LLM to generate CQL models. The machine learning network can be trained to convert a disease specific treatment algorithm into CQL models compatible to the FHIR system and for CDS hooks. The machine learning algorithm can be trained using historical information that include historical disease specific treatment algorithms, and resulting CQL models.

Training of models, such as artificial intelligence models, is necessarily rooted in computer technology, and improves modeling technology by using training data to train such models and thereafter applying the models to new inputs to make inferences on the new inputs. Here, the new inputs can be a disease specific treatment algorithm, EHR records specific to the patient, and/or new patient record updates.

Such training involves complex processing that typically requires a lot of processor computing and extended periods of time with large training data sets, which are typically performed by massive server systems. Training of models can require logistic regression and/or forward/backward propagating of training data that can include input data and expected output values that are used to adjust parameters of the models. Such training is the framework of machine learning algorithms that enable the models to be applied to new and unseen data (such as new patient data) and make predictions that the model was trained for based on the weights or scores that were adjusted during training. Such training of the machine learning models described herein reduces false positives and increases the performance of generating CQL models.

CQL models include a high-level, domain-specific language focused on clinical quality. These CQL models are designed to express logic that defines clinical concepts, triggers, data retrieval, and calculations in a standardized manner.

The CQL models generated by the LLM are FHIR-compatible. FHIR is a standard for health care data exchange that describes data formats and elements and an application programming interface (API) for exchanging electronic health records.

Thus in operation 104, the LLM processes the disease specific treatment algorithm and translates it into a CQL model that conforms with the FHIR standards and is compatible with the FHIR system. This involves understanding the disease specific treatment algorithm's logic, extracting the necessary information, and translating it into a format and structure that can be understood by the FHIR system.

This allows for the seamless exchange and application of this information in the context of healthcare data systems.

In some embodiments, the information received from the various data sources can be of a different format. Moreover, terms can be used differently by physicians. For example, one term can be referred to for different treatments or diseases. In another example, there can be multiple terms referring to the same treatment or diseases. The AI system can configure data from multiple different databases that are in their own non-standardized format into a single standardized format. As such, messages, queries, assessments, and alerts can be generated to communicate with physicians because the CQL models are using standardized format. Moreover, assessments and decisioning made by the AI system can be applied back to physicians by reapplying non-standardized formatting of the physician.

At operation 106, the AI system receives one or more CQL models from the LLM based on the processing of the data corresponding to the disease specific treatment algorithm. In FIG. 2, the AI system 210 processes the disease specific treatment algorithm 208 via the LLM 212 and receives one or more CQL models 214 from the LLM 212.

FIG. 2 illustrates the AI system 210 receiving a patient's EHR records 216. The EHR records 216 can also be applied to the LLM 212. The LLM 212 is trained to pull and/or apply the EHR records 216 from the EHR system 206 to the generated CQL models in order to determine whether to trigger a CDS hook. In some cases, the EHR records 216 are applied by a processor of the AI system 210 to the CQL models after the LLM 212 generates the CQL models.

Although examples herein are described as the LLM processing the EHR records using the CQL for simplicity, it is appreciated that the AI system can process the EHR records using the CQL models outputted by the LLM, and vice versa.

The LLM 212 can be trained to identify characteristics in the EHR records 216 to identify information relevant to the CQL model, such as characteristics that are relevant for diabetes. The CQL model provides recommendations or alerts based on a specific patient's medical history and current health status. For example, if a patient's HbA1c levels are rising despite oral medication, the CQL model may generate a CDS hook leading to a recommendation for the physician to consider insulin therapy.

In some examples, the LLM 212 is trained to apply demographic characteristics of the EHR records, such as age or race, which can affect the treatment or dosage amount of a certain medication.

In some cases, the EHR records include recordings directly from medical devices or from prior measurements. For example, the EHR records can include ECG readings directly from the Electrocardiogramar from a previous measurement of ECG recorded into the EHR records. The EHR records can include physiological characteristics measured by a physician. For example, the EHR records can include sphygmomanometer readings which measure blood pressure, thermometer readings used to measure body temperature, pulse oximeter to measure the saturation of oxygen in a patient's blood and pulse rate, glucometer used to measure the concentration of glucose in the blood, spirometer which measures lung capacity and volume, and/or the like.

In some cases, the AI system retrieves the patient's EHR from the same EHR system can provided the disease specific treatment algorithm and/or from the same medical facility treating the patient. In some cases, the AI system retrieves additional patient EHR data from other EHR systems, such as the patient's other associated health facilities. For example, the first EHR system can include a family care physician who provided the disease specific treatment algorithm, but the AI system may retrieve additional information from a radiologist or an ophthalmologist that the patient is or has visited in the past.

The AI system not only pulls medical records from the current physician's office that requested the CQL model, but also other servers corresponding to other health care facilities in the patient's network to get a full picture of the patient's medical condition. This in turn provides the LLM all of the potentially relevant information to provide the best CQL model custom tailored to the patient.

In some cases, the patient's EHR includes a digital version of a paper chart of an assessment by a medical practitioner of the patient. In some cases, the patient's EHR indicates a plurality of diseases and/or treatments. The LLM is trained to generate one or more treatments based on the plurality of disease and/or treatments. For example, a patient can have 15 diseases and takes 13 drugs. However, it may be difficult to keep track of how much or how often a type of drug should be administered, especially given the other diseases and drugs the patient is taking. The LLM is trained to reference the guidelines and provide a CQL model that keeps track of the drugs for the 15 diseases and triggers hooks for such complicated cases for physicians over certain periods of time.

In some cases, instructions and/or preferences are inputted into the LLM. The LLM can process these instructions and/or preferences to provide CQL models custom tailored to medical practitioners. For example, a CQL model preference tool is presented to the medical practitioner. The medical practitioner can provide customizations to such CQL models, such as preferences in certain disease scenarios, specific preferences for an individual patient or the general practice guidelines for the medical practitioner's approach to certain scenarios. Such customizations are considered by the LLM to generate CQL models that are specific to the medical practioner's preferences.

Generating Alerts Based on Updates to Patient Records

At operation 108, the AI system receives an update to a patient record of the patient from the first EHR system. At operation 110, the AI system receives preferences from physicians regarding CDS hook customizations. As further described herein, the alert can be transmitted based on a customization provided by the physician, such as the type, timing, communication channel, content, and/or triggers for the alerts.

At operation 112, the AI system, basing on the update and/or change to the patient record and the one or more expression logic models, triggers a CDS hook to generate an alert for the physician. The AI system identifies the delta of what has changed from a prior patient record and/or from what was expected in the patient record, such as a prescription of a drug, an expected update in new measurements in blood, and/or the like.

Figure 3:
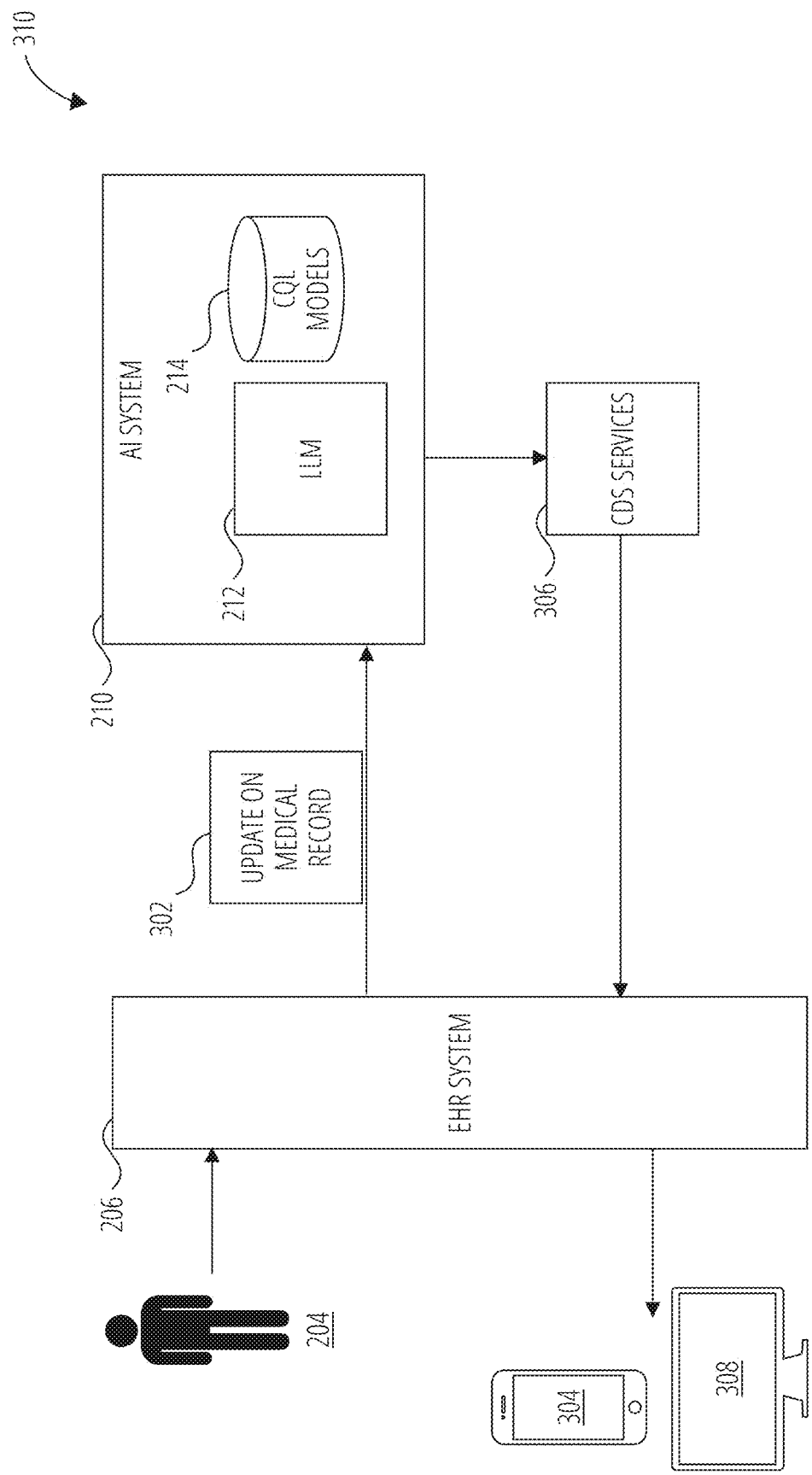
FIG. 3 illustrates an architecture of generating alerts based on updates to a patient record, according to some examples.

FIG. 3 illustrates an architecture 310 of generating alerts based on updates to a patient record, according to some examples. The EHR system 206 continues to record medical records over time of the patient 204. The EHR system 206 transmits updates to the medical record 302 to the AI system 210. The AI system 210 then applies the CQL models 214.

The CQL models 214 process the updates to the medical record 302 to determine whether to trigger a CDS hook. If the CQL model 214 determines to trigger a CDS hook, the AI system 210 invokes the remote service of the CDS services 306. The CDS services generates "CDS cards" that include information to be displayed to the physician.

At operation 114, the AI system causes transmission of the alert for a medical practitioner associated with the first EHR system. The AI system causes such transmission by invoking the remote service as shown in FIG. 2. The CDS services generate CDS cards to send to the EHR system 206. The EHR system then displays such alerts to the physician via the physician's computing devices, such as the physician's mobile phone 304 or a desktop 308.

In some cases, the LLM is trained to retrieve a patient's EHR and apply the patient's EHR to the one or more CQL models to generate one or more treatment procedures for the patient. Updates of the patient records are applied to the one or more treatment procedures. In some cases, the CDS hooks are triggered based on a failure to follow one or more treatment procedures, such as prescribing the correct dosage of a medication, failure in the update to the patient record to prescribe a medication at a particular time, other failures in one or more treatment procedures, and/or the like.

In some cases, the CDS hooks are triggered based on an indication of a newly prescribed medication in the update to the patient record, an indication of a new patient record opened in the update to the patient record, other new artifacts in the patient record, and/or the like. In the example of a newly prescribed medication, the CQL model can trigger CDS hooks such as an information card that includes how much the prescription costs per month (e.g., $45/m) and/or how much a patient would have to pay out of pocket (e.g., $7/m).

In some cases, the AI system retrieves data from other third party databases, such as insurance information of the patient from an insurance provider, medication data from pharmacies, and/or the like. Such data can be applied by the LLM or the CQL models (such as to generate the CQL models and/or determine whether to trigger a CDS hook).

In some cases, the CQL model triggers CDS hooks after reviewing patient records in certain periods of times. For example, for a particular patient, the recommended treatment can be to prescribe a certain drug periodically (such as monthly). The CQL model assesses updates to the patient records and determines that a drug was not prescribed within a certain time frame. The CQL model can invoke a CDS hook that could generate a reminder to the physician to order the drug for the patient.

In some cases, the CQL model can trigger CDS hooks such as a suggestion card, suggesting a different medication. In some cases, the trigger CDS hooks sending a suggestion card can provide an explanation, such as changing to a different medication due to the patient's age.

In some cases, the alert includes a user selectable interface element. In response to a user selection of the user selectable interface element, the AI system initiates communication with a third party server. For example, the AI system can communicate with a pharmacy to create, update, modify, or cancel a medication request.

In the suggestion card example mentioned above, a different drug is recommended. The alert can include a user selectable interface element that says "switch to new drug." In response to a user selection of the user selectable interface element, the AI system communicates with the pharmacy to change the drug order to the new recommended drug.

In some cases, the card, upon receipt from the EHR system, initiates opening of the physician's digital notes for the patient and enters in the alert such that the contents of the alert would not be a part of the patient's file in the EHR system. When the physician opens the file for the patient, the contents of the alert can be visible in conjunction with other information related to the patient.

In some cases, the cards include a smart app card that includes a link to initiate opening of an application and/or automatically initiates an application that is not currently open on the physician's device.

In some cases, the physician provides an indication of a preference for alerts provided to the physician. The physician can provide a preferred communication channel, such as a text, call, email, and/or the like. The physician can indicate a preference to not send or to send certain types of reminders, such as periodic reminders for medication. In some cases, a CDS hooks configuration tool is presented to a medical practitioner. The CDS hooks configuration tool enables a user to configure what types of cards are presented, when the cards can and/or should be presented, what type of content the cards should present, and/or the like. This preference enables custom tailored CDS hooks to be presented to the physician.

In some cases, the AI system retrains the LLM based on updates to the FHIR guidelines. For example, the AI system can retrain the LLM based on checking whether updates have been made on a periodic basis and/or retrain the LLM immediately upon determining a change has been made. In some cases, the AI system trains a completely new LLM based on updates to the FHIR guidelines.

In some cases, the AI system provides a comprehensive, full-focused healthcare framework that harnesses machine learning and natural language processing (NLP) to integrate seamlessly with Fast Healthcare Interoperability Resources (FHIR) and blockchain technology, realtime updates, enhancing interoperability and data security.

In some cases, the AI system implements electronic personalized profiles through the creation of electronic personalized profiles accessible across all patient devices, enabling real-time, secure transmission of patient data from electronic medical records (EMRs) to mobile devices in FHIR-compatible formats.

In some cases, the AI system implements NLP-Enhanced FHIR interfaces by utilizing NLP to establish FHIR interfaces that ensure seamless interoperability across all smart devices and existing EMRs, personal health records, and patient portals enhancing data exchange and patient care coordination by focusing on context specific CDS artifacts for patient education and advise In some cases, the AI system implements touchless sensors & IoT integration by conversion of electromagnetic waveform perturbations from touchless sensors into FHIR-compatible content, enabling comprehensive monitoring by EMRs or FHIR servers via IoT-enabled devices. This allows for real-time, remote monitoring of patient status and early detection of adverse events useful in phase 1 and 2 research trials as well as remote monitoring for home bound individuals with subacute or chronic diseases In some cases, the AI system implements global FHIR CQL repository by establishing a global repository that accepts, validates, and compensates personalized Clinical Quality Language (CQL) submissions. This repository would use this content to deliver intelligently generated smart applications on demand, facilitating the sharing of validated artifacts with clinicians in or outside formal networks.

In some cases, the AI system supports advanced research capabilities where EMR data and text notes would be converted into FHIR-compatible content that's mapped and transmitted to sponsors and research platforms such as CRIO. Investigators can have access to information in health information exchanges, government, pharmacy or research platforms.

The AI system can provide intelligent educational needs assessments by analyzing physician decisions; while also automatically suggesting targeted support artifacts for CDS hooks deployment in their electronic medical records/workflows or recommendations for CME delivered with a click.

In some cases, the AI system implements augment inclusion/exclusion decisions in clinical research by retrieval of FHIR based medical histories from health information exchanges to be used to intelligently design decisions support for investigators.

Training of the LLM

Figure 4:
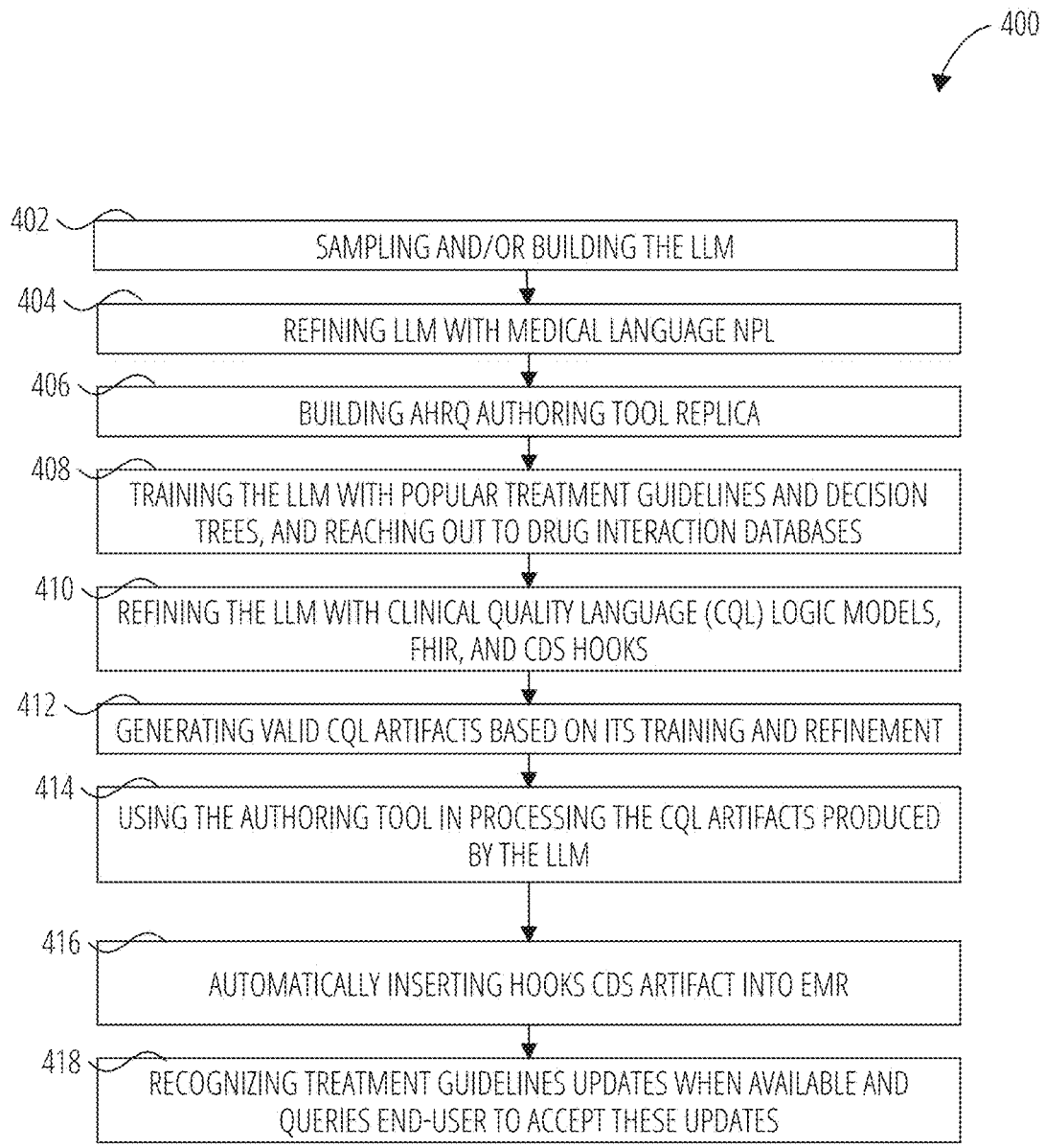
FIG. 4 illustrates an example method for training and applying the LLM, according to some examples.

FIG. 4 illustrates an example method 400 for training and applying the LLM, according to some examples. Although the example method 400 depicts a particular sequence of operations, the sequence may be altered without departing from the scope of the present disclosure. For example, some of the operations depicted may be performed in parallel or in a different sequence that does not materially affect the function of the method 400. In other examples, different components of an example device or system that implements the method 400 may perform functions at substantially the same time or in a specific sequence.

At operation 402, the AI system samples and/or builds the LLM. The AI system chooses an existing LLM or creates a new one. The AI system can select an appropriate pre-trained model, which can be a good starting point, one that is already trained to understand general language patterns. Such models can be further fine-tuned for specific tasks using additional training data.

If a new model is to be built, The AI sets up the LLM architecture (number of layers, number of nodes in each layer, activation functions etc.) and then training this model from scratch on a large dataset.

At operation 404, the AI system refines the LLM by training the LLM with medical language NPL. The AI system refines the LLM with Medical Language NLP by fine-tuning the model to better understand and process medical language. Medical language can be quite different from common language due to its specific terms, abbreviations, and phrase structures.

The refinement process involves training the model on medical datasets, which may include electronic health records, medical literature, clinical trial reports, etc. This allows the LLM to understand medical terminology, recognize the context in which terms are used, understand complex medical sentences, and make accurate predictions or classifications based on these inputs.

This process enhances the LLM's ability to process and analyze medical data accurately, thereby increasing its effectiveness in generating meaningful and accurate CQL models and other outputs.

At operation 406, the AI system builds an Agency for Healthcare Research and Quality (AHRQ) authoring tool replica. The AHRQ (Agency for Healthcare Research and Quality) is a part of the U.S. Department of Health and Human Services that is dedicated to improving the safety and quality of America's healthcare system. As part of its efforts, the AHRQ provides various tools and resources that are used by healthcare providers and researchers, including tools for creating, sharing, and implementing CDS systems.

The AI system builds an AHRQ authoring tool replica, which includes a software tool that mimics the functionality of an authoring tool provided by AHRQ. The authoring tool is used to create, edit, and manage clinical guidelines and protocols, which are then used within a CDS system to assist healthcare providers in making decisions about patient care.

Building a replica of an AHRQ authoring tool involves creating a new software tool that provides similar functionality. This could include features such as creating and editing clinical guidelines, converting guidelines into a format that can be used within a CDS system (such as CQL), managing the sharing and implementation of guidelines, and other related tasks.

This tool is then be integrated into the AI system, allowing the LLM to generate and manage CQL models based on the disease-specific treatment algorithms it is trained on.

At operation 408, the AI system trains the LLM with popular treatment guidelines and decision trees, and reaches out to drug interaction databases. The AI system feeds the LLM with well-established and widely-accepted treatment guidelines for various diseases. This allows the LLM to understand the standard procedures, treatments, and protocols followed in real-world medical scenarios.

Treatment guidelines, often formulated by medical experts and health organizations, provide detailed protocols to manage a particular disease. These guidelines can be seen as a series of decision trees-based on the current state of a patient, a decision (like prescribing a specific drug or running a particular test) is made, which further leads to other decisions.

Training the LLM on such guidelines helps the LLM to recognize the patterns and decision-making process in these guidelines, thus helping it to make similar decisions when faced with actual patient data.

At the same time, drug interaction databases are utilized to inform the LLM about the possible interactions between different drugs. This is critical information as certain combinations of drugs can lead to adverse effects. By integrating this information into its learning, the LLM can also consider drug interactions when providing recommendations or alerts.

The goal of this portion of the training is for the LLM to effectively replicate the decision-making process of a healthcare professional by using the given disease treatment guidelines and the knowledge about potential drug interactions.

At operation 410, the AI system refines the LLM with CQL logic models, FHIR, and CDS hooks. In this step, the LLM, which has already been trained on treatment guidelines and drug interaction databases, is further refined or fine-tuned using additional datasets and models.

CQL logic models are used to express the logic that defines measure populations and data criteria in a clear, consistent, and unambiguous manner. This information can help the LLM to understand the various standards used in healthcare and use these standards to make accurate predictions.

FHIR is a standard for health care data exchange. It is a protocol for exchanging healthcare information electronically. FHIR resources and data models can help the LLM to better understand the structure and semantics of healthcare data, improving its ability to work with such data and generate useful insights that are interoperable with FHIR features and functions.

CDS Hooks are a method for a clinical decision support system (like the AI system) to provide decision support directly within a clinician's workflow. By refining the LLM with CDS hooks, the LLM can better learn how to integrate and deliver its predictions in a way that fits seamlessly into a clinician's workflow, improving the usability and effectiveness of the LLM.

The goal of this refinement step is to enhance the LLM's understanding of clinical logic, healthcare data structures, and how to effectively deliver decision support, improving its performance and reliability in real-world settings.

At operation 412, the LLM generates valid CQL artifacts based on its training and refinement. The LLM builds valid CQL artifacts for the authoring tool. In this stage, the LLM, now trained and refined, is used to create representations of clinical logic (like patient care guidelines or rules for healthcare decision-making) encoded in the CQL. An "artifact" in this context is a unit of CQL code, containing clinical logic that can be applied to patient data to drive clinical decisions or evaluate quality measures. Examples might include code to check whether a patient with a particular set of symptoms and history should be given a certain medication, or to assess whether care provided in a certain case met established guidelines.

In this step, the LLM doesn't just produce any CQL artifacts—but "valid" artifacts, meaning they are correctly formed according to the CQL syntax and are logically sound, thus can be effectively used in the subsequent clinical decision support (CDS) processes. These artifacts are built for the "authoring tool" which is the software application that allows clinicians, clinical informationists, or other healthcare professionals to create, test, and validate CQL artifacts for use in a clinical setting.

At operation 414, the AI system uses the authoring tool in processing the CQL artifacts produced by the LLM. After the LLM has generated valid CQL artifacts, the authoring tool processes these artifacts to produce CDS artifacts. CDS artifacts are the applied forms of the CQL artifacts that guide clinical decision-making. They can be rules, alerts, order sets, dashboards, etc., designed to provide patient-specific information to clinicians at the point of care.

This step emphasizes the dynamic nature of these CDS artifacts. Users can customize cards (user interface elements that provide specific information or prompt particular actions), and define trigger events (the specific circumstances or patient characteristics that prompt the presentation of a CDS card to the clinician).

In operation 416, the AI system automatically inserts hooks into the EMR by integrating the generated CDS artifacts into EMRs. Once the authoring tool has produced valid CDS artifacts, these need to be integrated into the EMR systems used by clinicians.

The AI system inserts these CDS artifacts to inject the decision support directly into the EMR. For example, when a certain event happens within the EMR (e.g., a clinician opens a patient's record or orders a medication), the hook triggers the relevant CDS artifact. This provides the clinician with contextually relevant decision support (such as alerts or recommendations) exactly when and where it is needed.

The AI system inserts these CDS artifacts without manual intervention or support from an IT department. This could be an important feature for healthcare organizations, as it could save time and resources and reduce the potential for errors in the integration process. Automated integration also ensures that the most current CDS artifacts are always available within the EMR. This seamless integration of CDS into the workflow of clinicians is crucial for the effective use of these decision support tools.

At operation 418, the AI system recognizes treatment guidelines updates when available and queries end-user to accept these updates. In this step, the AI system updates the CDS tools with new treatment guidelines, as they become available. This step signifies the capability of the AI system to stay current with the ever-evolving landscape of medical knowledge. The AI system keeps track of updates to treatment guidelines, which are often revised based on new scientific evidence or updated clinical standards.

When the AI identifies an update to a treatment guideline that it has been trained on, the AI system revises the corresponding CQL model and CDS hooks accordingly. However, before these changes are implemented, the system queries or prompts the end-user (likely a healthcare provider or a medical professional) to accept these updates.

This approach ensures that the CDS tools used by healthcare providers are always up-to-date with the latest evidence-based practices. By querying the end-user to accept, the AI system also ensures that healthcare providers have the final say in the CDS recommendations, maintaining a human in the loop for the sake of safety and to account for the nuances of individual patient care.

This continuous learning and updating is a critical component of the AI system, especially in the field of healthcare where new research and evidence continually evolve the understanding and best practices of patient care.

Application of the LLM

Figure 5:
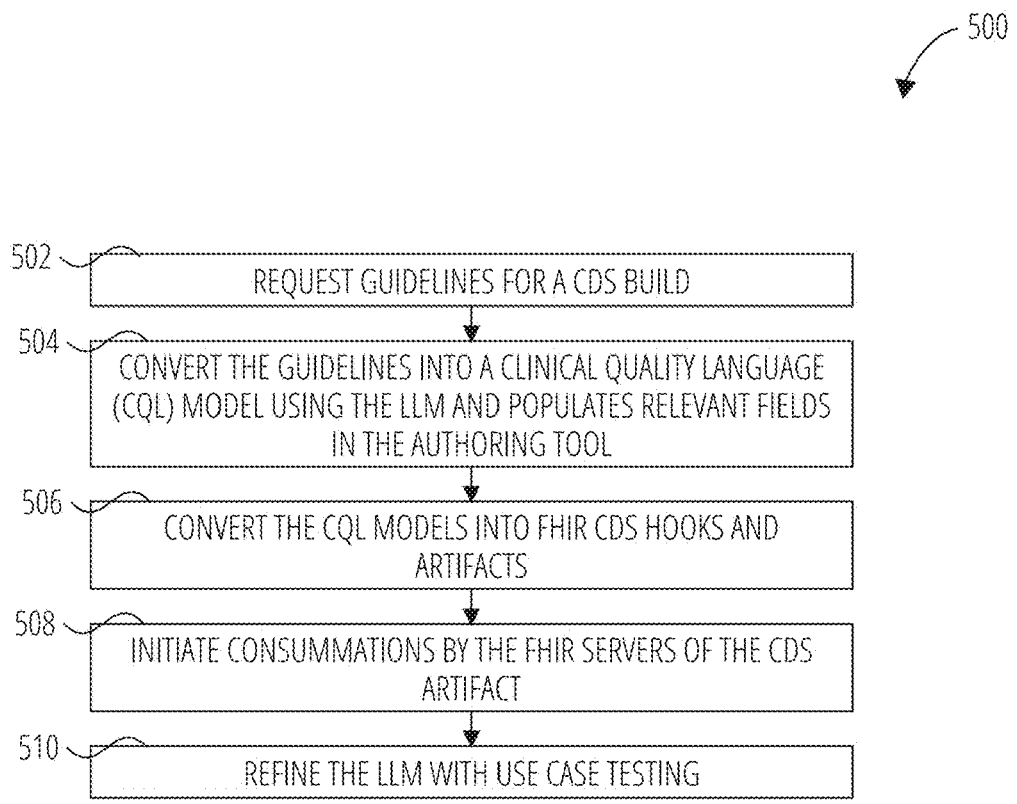
FIG. 5 illustrates a method for applying the LLM once the LLM has been trained, according to some examples.

FIG. 5 illustrates a method 500 for applying the LLM once the LLM has been trained, according to some examples. At operation 502, the user requests guidelines for a CDS build, which initiates of the CDS system building process. A user (likely a healthcare provider or an administrator) requests guidelines for building a CDS system. These guidelines outline the best practices, actions, and considerations to make when treating a specific condition or disease.

The AI system trains the LLM on the required NLP and medical language tasks (as further described herein). It uses a "medical corpus", which is a large and structured set of texts around medical knowledge, as its training data. The purpose of this training is to enable the LLM to understand and generate medical language effectively.

The LLM also uses an "encoder" to transform primary care guidelines into a more accessible and processable format. The encoder is a component of the LLM that converts input data (such as primary care guidelines) into a different format or representation. This conversion is crucial for the LLM to interpret and manipulate the guidelines in subsequent steps of the process.

At operation 504, the AI system converts the guidelines into a CQL model using the LLM and populates relevant fields in the Authoring tool. This phase begins with the transformation of the disease-specific treatment guideline, initially received as input by the AI, into a CQL model. The AI system can leverage an already available CQL framework, which is a tool or library that aids in creating, editing, and executing CQL statements.

Once the guideline has been transformed into a CQL model, the AI system populate relevant fields in a cloned version of the AHRQ authoring tool. The AI, which has been trained on medical language and clinical guidelines, can identify relevant data from the CQL model and use it to fill out the appropriate sections of the authoring tool. This step is vital for creating a valid CDS artifact (i.e., a piece of data or a set of rules that can be used to support clinical decisions) that can be used in the next steps of the process.

At operation 506, the AI system converts the CQL models into FHIR CDS hooks and artifacts. The CQL models, which were previously derived from treatment guidelines and then populated in the authoring tool by the AI, are transformed into FHIR CDS hooks. These hooks provide a way to send notifications (such as patient-view or medication-prescribe)

to external services. These services can then provide decision support, returning actionable information back to the EHR or AI system.

The CQL model to CDS hooks transformation is performed by coding the clinical logic and guidelines in the CQL models that are now encapsulated within interoperable FHIR artifacts, making them actionable within a healthcare system's EHR.

The AI system asks users (such as healthcare providers or clinical informationists) to configure these CDS hook artifacts to best fit their needs. This could include specifying what kind of cards are shown, when and how these cards are triggered, and fine-tuning other details about how the decision support tools operate in their specific clinical environment. This ensures that the CDS system provides the most useful and relevant assistance possible.

At operation 508, the AI system initiates consummations by the FHIR servers of the CDS artifact. In this step, the CDS artifacts, which were created from the CQL and tailored by users in the previous step, are now consumed by a FHIR server. The CDS artifacts are loaded into the FHIR server.

Once this is done, the decision support system can now invoke these CDS services in response to relevant events within the EHR system. For example, when a physician prescribes medication to a patient, the CDS hook could be invoked to check for potential drug-drug interactions or contraindications based on the patient's health record, and present relevant notifications or alerts back to the physician.

At operation 510, the AI system refines the LLM with use case testing. After the CDS artifacts are loaded into the FHIR server and the server is set up, the AI system tests the whole system and refine it based on feedback and test results.

The AI system tests the LLM and the other modules for real-world use cases to ensure that the system behaves as expected in the specific scenarios that it will encounter once deployed in a clinical setting. This might involve feeding it with example patient records and observing if the right CDS hooks are generated and if they successfully trigger the appropriate responses.

In some cases, the AI system tests the system with a subset of the target audience. These users will use the AI system in a real-world setting and provide feedback. This feedback can be invaluable to understand how the system behaves in real-world conditions and make necessary improvements.

In some cases, the AI system measures the effectiveness of the LLM and other modules by measuring the accuracy of its predictions, collecting user satisfaction surveys, or using tools to evaluate its impact on clinical outcomes.

This phase is crucial as it allows for adjustments and improvements to the AI system before it is fully deployed, based on real-world testing and feedback. This also helps ensure the system's effectiveness and reliability, reducing the risk of issues after full-scale deployment.

Machine Architecture

Figure 6:
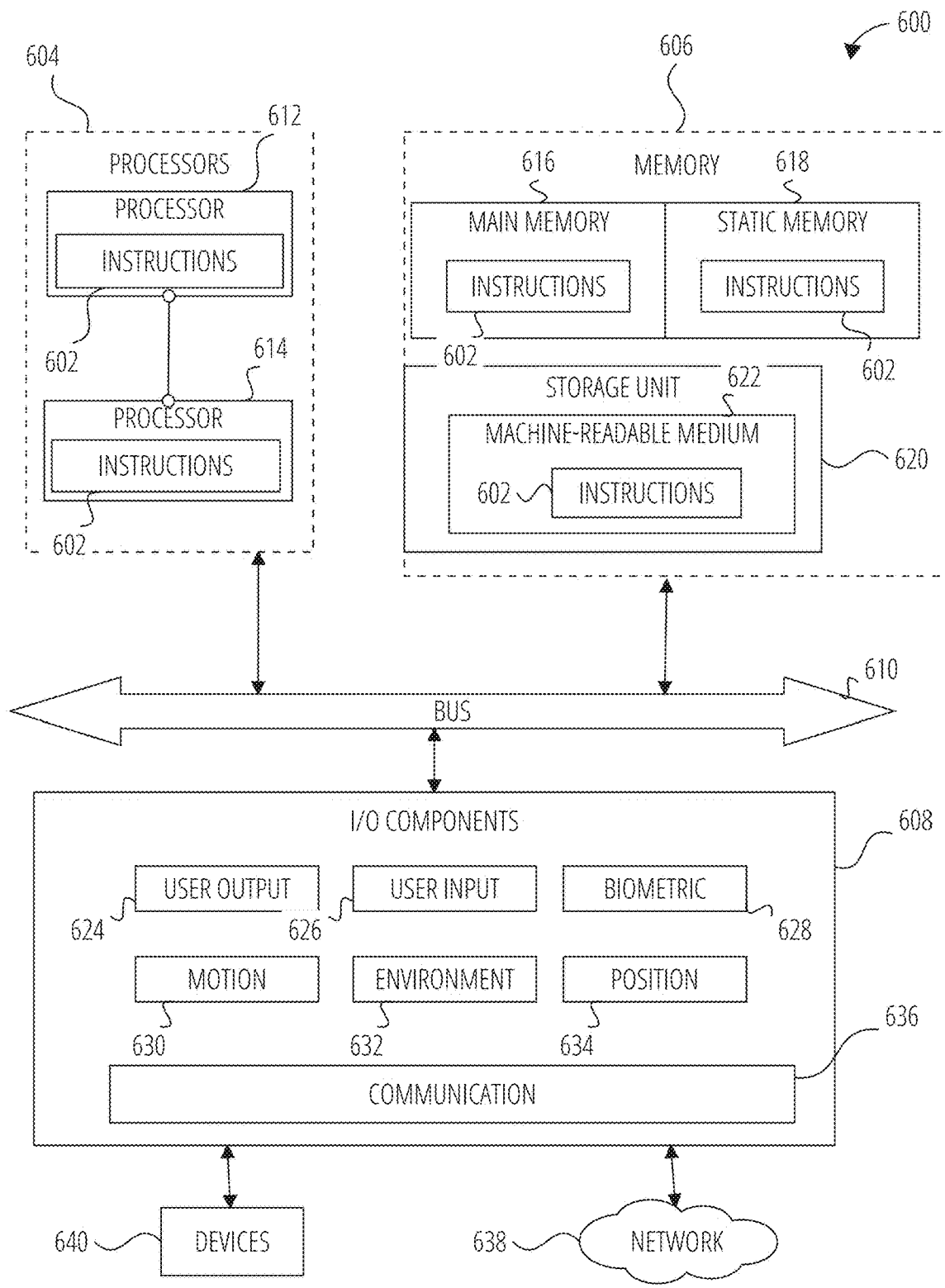
FIG. 6 is a diagrammatic representation of a machine in the form of a computer system within which a set of instructions may be executed to cause the machine to perform any one or more of the methodologies discussed herein, according to some examples.

FIG. 6 is a diagrammatic representation of the machine 600 within which instructions 602 (e.g., software, a program, an application, an applet, an app, or other executable code) for causing the machine 600 to perform any one or more of the methodologies discussed herein may be executed. For example, the instructions 602 may cause the machine 600 to execute any one or more of the methods described herein. The instructions 602 transform the general, non-programmed machine 600 into a particular machine 600 programmed to carry out the described and illustrated functions in the manner described. The machine 600 may operate as a standalone device or may be coupled (e.g., networked) to other machines. In a networked deployment, the machine 600 may operate in the capacity of a server machine or a client machine in a server-client network environment, or as a peer machine in a peer-to-peer (or distributed) network environment. The machine 600 may comprise, but not be limited to, a server computer, a client computer, a personal computer (PC), a tablet computer, a laptop computer, a netbook, a set-top box (STB), a personal digital assistant (PDA), an entertainment media system, a cellular telephone, a smartphone, a mobile device, a wearable device (e.g., a smartwatch), a smart home device (e.g., a smart appliance), other smart devices, a web appliance, a network router, a network switch, a network bridge, or any machine capable of executing the instructions 602, sequentially or otherwise, that specify actions to be taken by the machine 600. Further, while a single machine 600 is illustrated, the term "machine" shall also be taken to include a collection of machines that individually or jointly execute the instructions 602 to perform any one or more of the methodologies discussed herein. The machine 600, for example, may comprise a user system or any one of multiple server devices forming part of the server system. In some examples, the machine 600 may also comprise both client and server systems, with certain operations of a particular method or algorithm being performed on the server-side and with certain operations of the particular method or algorithm being performed on the client-side.

The machine 600 may include processors 604, memory 606, and input/output I/O components 608, which may be configured to communicate with each other via a bus 610. In an example, the processors 604 (e.g., a Central Processing Unit (CPU), a Reduced Instruction Set Computing (RISC) Processor, a Complex Instruction Set Computing (CISC) Processor, a Graphics Processing Unit (GPU), a Digital Signal Processor (DSP), an Application Specific Integrated Circuit (ASIC), a Radio-Frequency Integrated Circuit (RFIC), another processor, or any suitable combination thereof) may include, for example, a processor 612 and a processor 614 that execute the instructions 602. The term "processor" is intended to include multi-core processors that may comprise two or more independent processors (sometimes referred to as "cores") that may execute instructions contemporaneously. Although FIG. 6 shows multiple processors 604, the machine 600 may include a single processor with a single-core, a single processor with multiple cores (e.g., a multi-core processor), multiple processors with a single core, multiple processors with multiples cores, or any combination thereof.

The memory 606 includes a main memory 616, a static memory 618, and a storage unit 620, both accessible to the processors 604 via the bus 610. The main memory 606, the static memory 618, and storage unit 620 store the instructions 602 embodying any one or more of the methodologies or functions described herein. The instructions 602 may also reside, completely or partially, within the main memory 616, within the static memory 618, within machine-readable medium 622 within the storage unit 620, within at least one of the processors 604 (e.g., within the processor's cache memory), or any suitable combination thereof, during execution thereof by the machine 600.

The I/O components 608 may include a wide variety of components to receive input, provide output, produce output, transmit information, exchange information, capture measurements, and so on. The specific I/O components 608 that are included in a particular machine will depend on the type of machine. For example, portable machines such as mobile phones may include a touch input device or other such input mechanisms, while a headless server machine will likely not include such a touch input device. It will be appreciated that the I/O components 608 may include many other components that are not shown in FIG. 6. In various examples, the I/O components 608 may include user output components 624 and user input components 626. The user output components 624 may include visual components (e.g., a display such as a plasma display panel (PDP), a light-emitting diode (LED) display, a liquid crystal display (LCD), a projector, or a cathode ray tube (CRT)), acoustic components (e.g., speakers), haptic components (e.g., a vibratory motor, resistance mechanisms), other signal generators, and so forth. The user input components 626 may include alphanumeric input components (e.g., a keyboard, a touch screen configured to receive alphanumeric input, a photo-optical keyboard, or other alphanumeric input components), point-based input components (e.g., a mouse, a touchpad, a trackball, a joystick, a motion sensor, or another pointing instrument), tactile input components (e.g., a physical button, a touch screen that provides location and force of touches or touch gestures, or other tactile input components), audio input components (e.g., a microphone), and the like.

In further examples, the I/O components 608 may include medical device components 628, motion components 630, environmental components 632, or position components 634, among a wide array of other components. For example, the medical device components 628 include components to detect data from medical devices, as further described herein.

The motion components 630 include acceleration sensor components (e.g., accelerometer), gravitation sensor components, rotation sensor components (e.g., gyroscope).

The environmental components 632 include, for example, one or more cameras (with still image/photograph and video capabilities), illumination sensor components (e.g., photometer), temperature sensor components (e.g., one or more thermometers that detect ambient temperature), humidity sensor components, pressure sensor components (e.g., barometer), acoustic sensor components (e.g., one or more microphones that detect background noise), proximity sensor components (e.g., infrared sensors that detect nearby objects), gas sensors (e.g., gas detection sensors to detect concentrations of hazardous gasses for safety or to measure pollutants in the atmosphere), or other components that may provide indications, measurements, or signals corresponding to a surrounding physical environment.

The position components 634 include location sensor components (e.g., a GPS receiver component), altitude sensor components (e.g., altimeters or barometers that detect air pressure from which altitude may be derived), orientation sensor components (e.g., magnetometers), and the like.

Communication may be implemented using a wide variety of technologies. The I/O components 608 further include communication components 636 operable to couple the machine 600 to a network 638 or devices 640 via respective coupling or connections. For example, the communication components 636 may include a network interface component or another suitable device to interface with the network 638. In further examples, the communication components 636 may include wired communication components, wireless communication components, cellular communication components, Near Field Communication (NFC) components, Bluetooth® components (e.g., Bluetooth® Low Energy), Wi-Fi® components, and other communication components to provide communication via other modalities. The devices 640 may be another machine or any of a wide variety of peripheral devices (e.g., a peripheral device coupled via a USB).

Moreover, the communication components 636 may detect identifiers or include components operable to detect identifiers. For example, the communication components 636 may include Radio Frequency Identification (RFID) tag reader components, NFC smart tag detection components, optical reader components (e.g., an optical sensor to detect one-dimensional bar codes such as Universal Product Code (UPC) bar code, multi-dimensional bar codes such as Quick Response (QR) code, Aztec code, Data Matrix, Dataglyph™, MaxiCode, PDF417, Ultra Code, UCC RSS-2D bar code, and other optical codes), or acoustic detection components (e.g., microphones to identify tagged audio signals). In addition, a variety of information may be derived via the communication components 636, such as location via Internet Protocol (IP) geolocation, location via Wi-Fi® signal triangulation, location via detecting an NFC beacon signal that may indicate a particular location, and so forth.

The various memories (e.g., main memory 616, static memory 618, and memory of the processors 604) and storage unit 620 may store one or more sets of instructions and data structures (e.g., software) embodying or used by any one or more of the methodologies or functions described herein. These instructions (e.g., the instructions 602), when executed by processors 604, cause various operations to implement the disclosed examples.

The instructions 602 may be transmitted or received over the network 638, using a transmission medium, via a network interface device (e.g., a network interface component included in the communication components 636) and using any one of several well-known transfer protocols (e.g., hypertext transfer protocol (HTTP)). Similarly, the instructions 602 may be transmitted or received using a transmission medium via a coupling (e.g., a peer-to-peer coupling) to the devices 640.

Software Architecture

Figure 7:
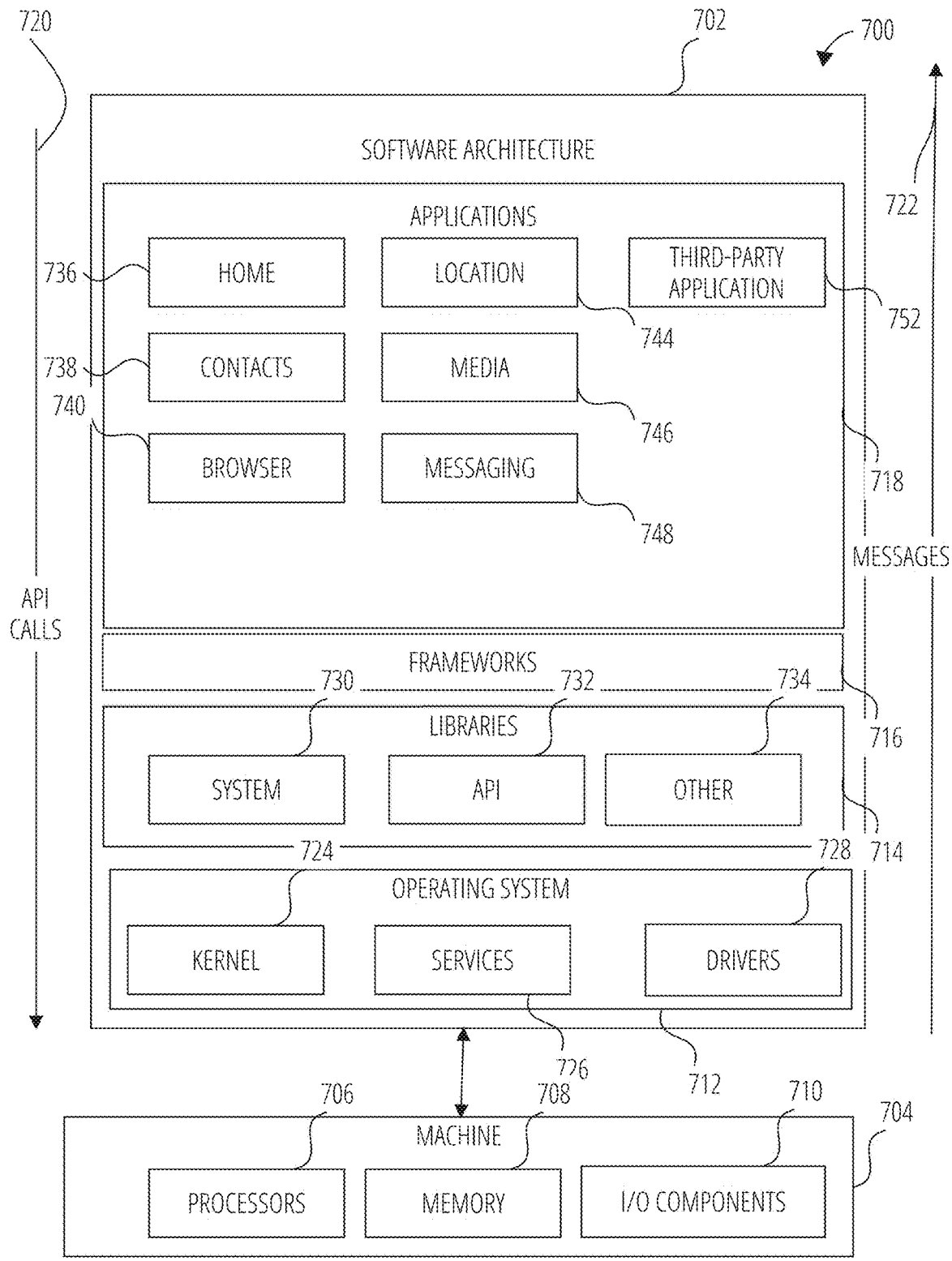
FIG. 7 is a block diagram showing a software architecture within which examples may be implemented.

FIG. 7 is a block diagram 700 illustrating a software architecture 702, which can be installed on any one or more of the devices described herein. The software architecture 702 is supported by hardware such as a machine 704 that includes processors 706, memory 708, and I/O components 710. In this example, the software architecture 702 can be conceptualized as a stack of layers, where each layer provides a particular functionality. The software architecture 702 includes layers such as an operating system 712, libraries 714, frameworks 716, and applications 718. Operationally, the applications 718 invoke API calls 720 through the software stack and receive messages 722 in response to the API calls 720.

The operating system 712 manages hardware resources and provides common services. The operating system 712 includes, for example, a kernel 724, services 726, and drivers 728. The kernel 724 acts as an abstraction layer between the hardware and the other software layers. For example, the kernel 724 provides memory management, processor management (e.g., scheduling), component management, networking, and security settings, among other functionalities. The services 726 can provide other common services for the other software layers. The drivers 728 are responsible for controlling or interfacing with the underlying hardware. For instance, the drivers 728 can include display drivers, camera drivers, BLUETOOTH® or BLUETOOTH® Low Energy drivers, flash memory drivers, serial communication drivers (e.g., USB drivers), WI-FI® drivers, audio drivers, power management drivers, and so forth.

The libraries 714 provide a common low-level infrastructure used by the applications 718. The libraries 714 can include system libraries 730 (e.g., C standard library) that provide functions such as memory allocation functions, string manipulation functions, mathematic functions, and the like. In addition, the libraries 714 can include API libraries 732 such as media libraries (e.g., libraries to support presentation and manipulation of various media formats such as Moving Picture Experts Group-4 (MPEG4), Advanced Video Coding (H.264 or AVC), Moving Picture Experts Group Layer-3 (MP3), Advanced Audio Coding (AAC), Adaptive Multi-Rate (AMR) audio codec, Joint Photographic Experts Group (JPEG or JPG), or Portable Network Graphics (PNG)), graphics libraries (e.g., an OpenGL framework used to render in two dimensions (2D) and three dimensions (3D) in a graphic content on a display), database libraries (e.g., SQLite to provide various relational database functions), web libraries (e.g., WebKit to provide web browsing functionality), and the like. The libraries 714 can also include a wide variety of other libraries 734 to provide many other APIs to the applications 718.

The frameworks 716 provide a common high-level infrastructure that is used by the applications 718. For example, the frameworks 716 provide various graphical user interface (GUI) functions, high-level resource management, and high-level location services. The frameworks 716 can provide a broad spectrum of other APIs that can be used by the applications 718, some of which may be specific to a particular operating system or platform.

In an example, the applications 718 may include a home application 736, a contacts application 738, a browser application 740, a location application 744, a media application 746, a messaging application 748, and a broad assortment of other applications such as a third-party application 752. The applications 718 are programs that execute functions defined in the programs. Various programming languages can be employed to create one or more of the applications 718, structured in a variety of manners, such as object-oriented programming languages (e.g., Objective-C, Java, or C++) or procedural programming languages (e.g., C or assembly language). In a specific example, the third-party application 752 (e.g., an application developed using the ANDROID™ or IOS™ software development kit (SDK) by an entity other than the vendor of the particular platform) may be mobile software running on a mobile operating system such as IOS™, ANDROID™, WINDOWS® Phone, or another mobile operating system. In this example, the third-party application 752 can invoke the API calls 720 provided by the operating system 712 to facilitate functionalities described herein.

Machine-Learning Pipeline

Figure 9:
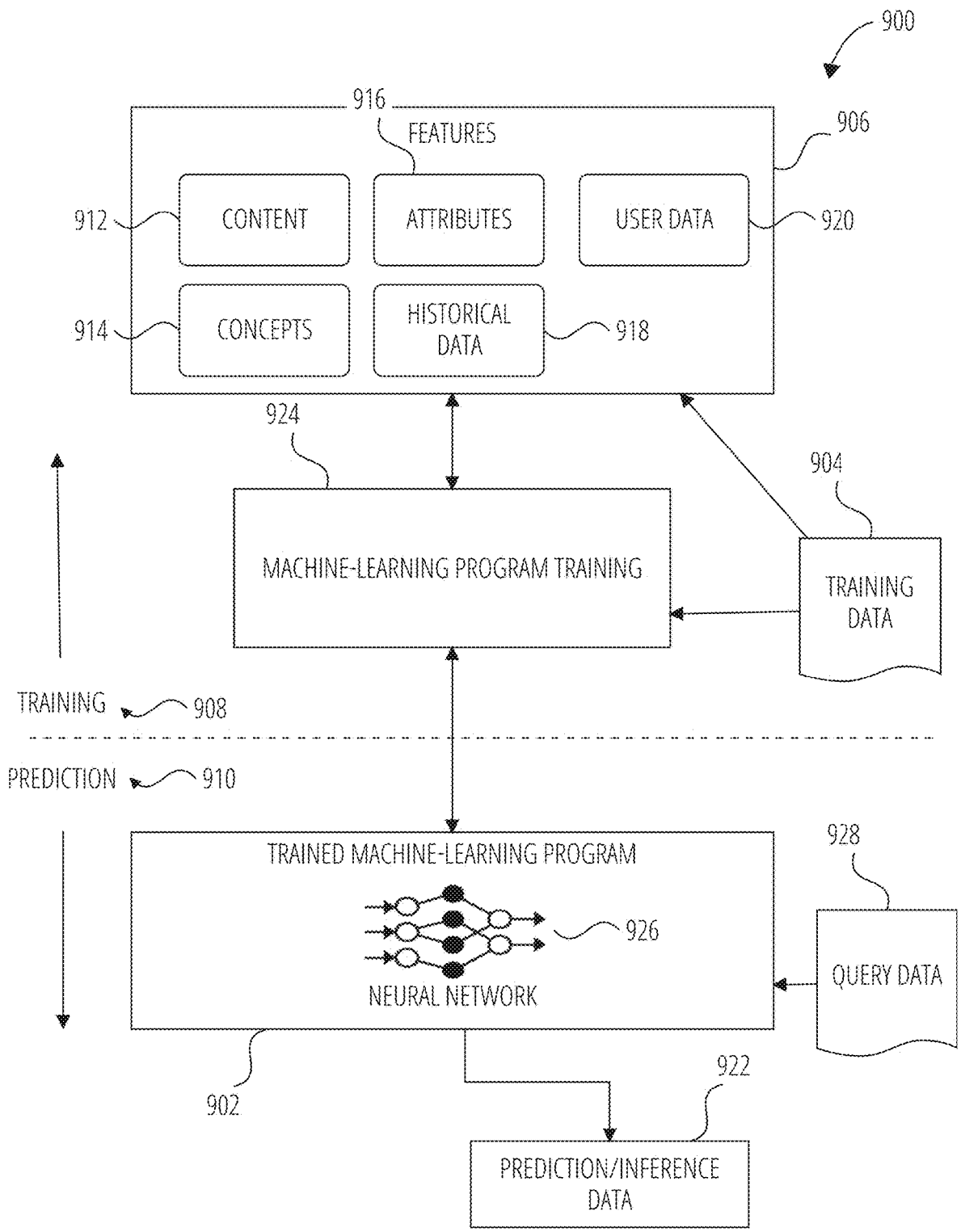
FIG. 9 illustrates training and use of a machine-learning program, according to some examples.

FIG. 9 is a flowchart depicting a machine-learning pipeline 900, according to some examples. The machine-learning pipelines 900 may be used to generate a trained model, for example the trained machine-learning program 902 of FIG. 9, described herein to perform operations associated with searches and query responses.

Overview

Broadly, machine learning may involve using computer algorithms to automatically learn patterns and relationships in data, potentially without the need for explicit programming to do so after the algorithm is trained. Examples of machine learning algorithms can be divided into three main categories: supervised learning, unsupervised learning, and reinforcement learning.

Supervised learning involves training a model using labeled data to predict an output for new, unseen inputs. Examples of supervised learning algorithms include linear regression, decision trees, and neural networks.

Unsupervised learning involves training a model on unlabeled data to find hidden patterns and relationships in the data. Examples of unsupervised learning algorithms include clustering, principal component analysis, and generative models like autoencoders.

Reinforcement learning involves training a model to make decisions in a dynamic environment by receiving feedback in the form of rewards or penalties. Examples of reinforcement learning algorithms include Q-learning and policy gradient methods.

Examples of specific machine learning algorithms that may be deployed, according to some examples, include logistic regression, which is a type of supervised learning algorithm used for binary classification tasks. Logistic regression models the probability of a binary response variable based on one or more predictor variables. Another example type of machine learning algorithm is Naïve Bayes, which is another supervised learning algorithm used for classification tasks. Naïve Bayes is based on Bayes' theorem and assumes that the predictor variables are independent of each other. Random Forest is another type of supervised learning algorithm used for classification, regression, and other tasks. Random Forest builds a collection of decision trees and combines their outputs to make predictions. Further examples include neural networks which consist of interconnected layers of nodes (or neurons) that process information and make predictions based on the input data. Matrix factorization is another type of machine learning algorithm used for recommender systems and other tasks. Matrix factorization decomposes a matrix into two or more matrices to uncover hidden patterns or relationships in the data. Support Vector Machines (SVM) are a type of supervised learning algorithm used for classification, regression, and other tasks. SVM finds a hyperplane that separates the different classes in the data. Other types of machine learning algorithms include decision trees, k-nearest neighbors, clustering algorithms, and deep learning algorithms such as convolutional neural networks (CNN), recurrent neural networks (RNN), and transformer models. The choice of algorithm depends on the nature of the data, the complexity of the problem, and the performance requirements of the application.

The performance of machine learning models is typically evaluated on a separate test set of data that was not used during training to ensure that the model can generalize to new, unseen data. Evaluating the model on a separate test set helps to mitigate the risk of overfitting, a common issue in machine learning where a model learns to perform exceptionally well on the training data but fails to maintain that performance on data it hasn't encountered before. By using a test set, the system obtains a more reliable estimate of the model's real-world performance and its potential effectiveness when deployed in practical applications.

Although several specific examples of machine learning algorithms are discussed herein, the principles discussed herein can be applied to other machine learning algorithms as well. Deep learning algorithms such as convolutional neural networks, recurrent neural networks, and transformers, as well as more traditional machine learning algorithms like decision trees, random forests, and gradient boosting may be used in various machine learning applications.

Two example types of problems in machine learning are classification problems and regression problems. Classification problems, also referred to as categorization problems, aim at classifying items into one of several category values (for example, is this object an apple or an orange?). Regression algorithms aim at quantifying some items (for example, by providing a value that is a real number).

Phases

Figure 8:
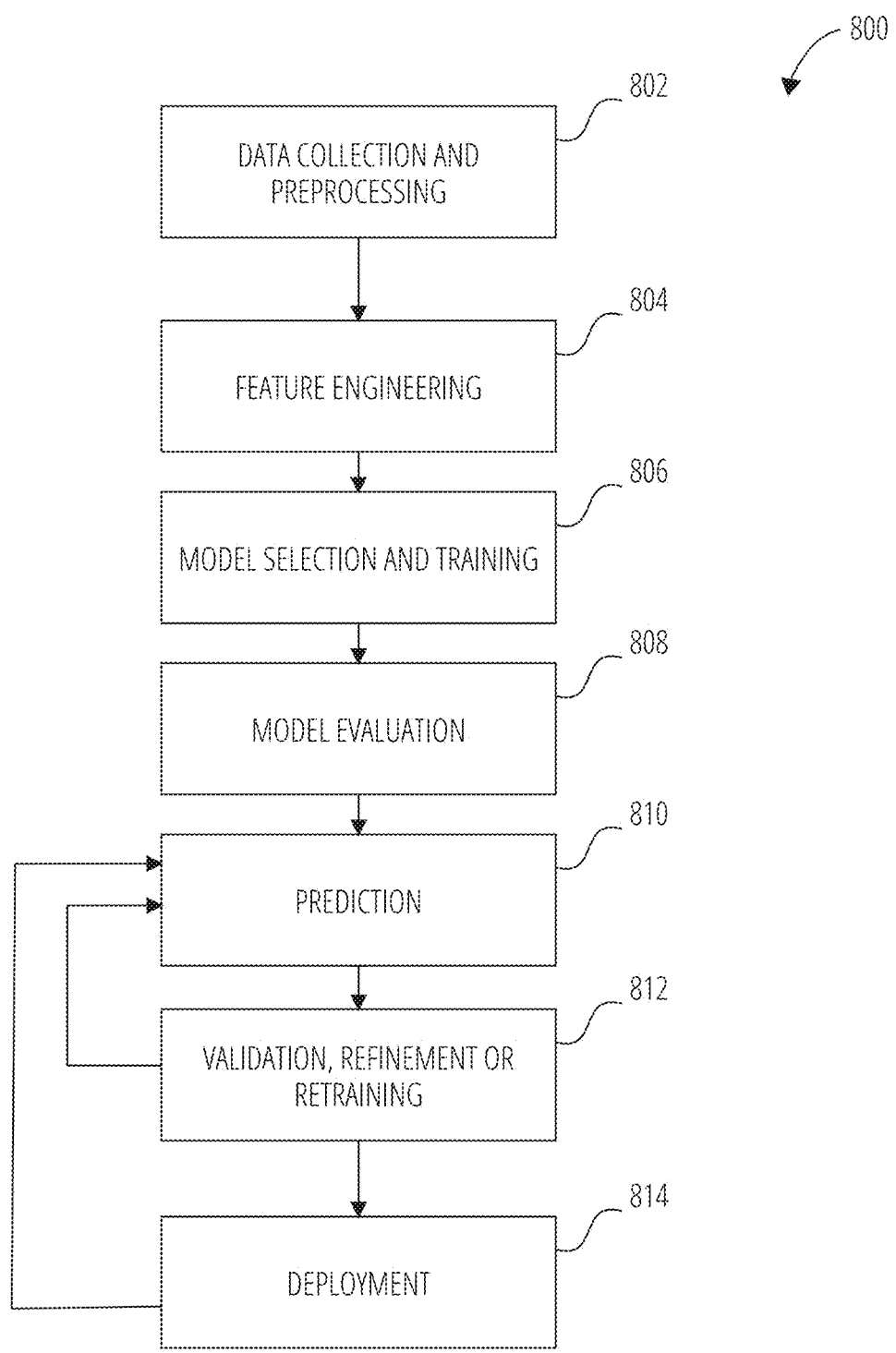
FIG. 8 illustrates a machine-learning pipeline, according to some examples.

Generating a trained machine-learning program 902 may include multiple types of phases that form part of the machine-learning pipeline 900, including for example the following phases 800 illustrated in FIG. 8:

Data collection and preprocessing 802: This may include acquiring and cleaning data to ensure that it is suitable for use in the machine learning model. Data can be gathered from user content creation and labeled using a machine learning algorithm trained to label data. Data can be generated by applying a machine learning algorithm to identify or generate similar data. This may also include removing duplicates, handling missing values, and converting data into a suitable format.

Feature engineering 804: This may include selecting and transforming the training data 904 to create features that are useful for predicting the target variable. Feature engineering may include (1) receiving features 906 (e.g., as structured or labeled data in supervised learning) and/or (2) identifying features 906 (e.g., unstructured or unlabeled data for unsupervised learning) in training data 904.

Model selection and training 806: This may include specifying a particular problem or desired response from input data, selecting an appropriate machine learning algorithm, and training it on the preprocessed data. This may further involve splitting the data into training and testing sets, using cross-validation to evaluate the model, and tuning hyperparameters to improve performance. Model selection can be based on factors such as the type of data, problem complexity, computational resources, or desired performance.

Model evaluation 808: This may include evaluating the performance of a trained model (e.g., the trained machine-learning program 902) on a separate testing dataset. This can help determine if the model is overfitting or underfitting and if it is suitable for deployment.

Prediction 810: This involves using a trained model (e.g., trained machine-learning program 902) to generate predictions on new, unseen data.

Validation, refinement or retraining 812: This may include updating a model based on feedback generated from the prediction phase, such as new data or user feedback.

Deployment 814: This may include integrating the trained model (e.g., the trained machine-learning program 902) into a larger system or application, such as a web service, mobile app, or IoT device. This can involve setting up APIs, building a user interface, and ensuring that the model is scalable and can handle large volumes of data.

FIG. 9 illustrates two example phases, namely a training phase 908 (part of the model selection and trainings 806) and a prediction phase 910 (part of prediction 810). Prior to the training phase 908, feature engineering 804 is used to identify features 906. This may include identifying informative, discriminating, and independent features for the effective operation of the trained machine-learning program 902 in pattern recognition, classification, and regression. In some examples, the training data 904 includes labeled data, which is known data for pre-identified features 906 and one or more outcomes.

Each of the features 906 may be a variable or attribute, such as individual measurable property of a process, article, system, or phenomenon represented by a data set (e.g., the training data 904). Features 906 may also be of different types, such as numeric features, strings, vectors, matrices, encodings, and graphs, and may include one or more of content 912, concepts 914, attributes 916, historical data 918 and/or user data 920, merely for example. Concept features can include abstract relationships or patterns in data, such as determining a topic of a document or discussion in a chat window between users. Content features include determining a context based on input information, such as determining a context of a user based on user interactions or surrounding environmental factors. Context features can include text features, such as frequency or preference of words or phrases, image features, such as pixels, textures, or pattern recognition, audio classification, such as spectrograms, and/or the like. Attribute features include intrinsic attributes (directly observable) or extrinsic features (derived), such as identifying square footage, location, or age of a real estate property identified in a camera feed. User data features include data pertaining to a particular individual or to a group of individuals, such as in a geographical location or that share demographic characteristics. User data can include demographic data (such as age, gender, location, or occupation), user behavior (such as browsing history, purchase history, conversion rates, click-through rates, or engagement metrics), or user preferences (such as preferences to certain video, text, or digital content items). Historical data includes past events or trends that can help identify patterns or relationships over time.

In training phases 908, the machine-learning pipeline 900 uses the training data 904 to find correlations among the features 906 that affect a predicted outcome or prediction/inference data 922.

With the training data 904 and the identified features 906, the trained machine-learning program 902 is trained during the training phase 908 during machine-learning program training 924. The machine-learning program training 924 appraises values of the features 906 as they correlate to the training data 904. The result of the training is the trained machine-learning program 902 (e.g., a trained or learned model).

Further, the training phase 908 may involve machine learning, in which the training data 904 is structured (e.g., labeled during preprocessing operations), and the trained machine-learning program 902 implements a relatively simple neural network 926 capable of performing, for example, classification and clustering operations. In other examples, the training phase 908 may involve deep learning, in which the training data 904 is unstructured, and the trained machine-learning program 902 implements a deep neural network 926 that is able to perform both feature extraction and classification/clustering operations.

A neural network 926 may, in some examples, be generated during the training phase 908, and implemented within the trained machine-learning program 902. The neural network 926 includes a hierarchical (e.g., layered) organization of neurons, with each layer including multiple neurons or nodes. Neurons in the input layer receive the input data, while neurons in the output layer produce the final output of the network. Between the input and output layers, there may be one or more hidden layers, each including multiple neurons.

Each neuron in the neural network 926 operationally computes a small function, such as an activation function that takes as input the weighted sum of the outputs of the neurons in the previous layer, as well as a bias term. The output of this function is then passed as input to the neurons in the next layer. If the output of the activation function exceeds a certain threshold, an output is communicated from that neuron (e.g., transmitting neuron) to a connected neuron (e.g., receiving neuron) in successive layers. The connections between neurons have associated weights, which define the influence of the input from a transmitting neuron to a receiving neuron. During the training phase, these weights are adjusted by the learning algorithm to optimize the performance of the network. Different types of neural networks may use different activation functions and learning algorithms, which can affect their performance on different tasks. Overall, the layered organization of neurons and the use of activation functions and weights enable neural networks to model complex relationships between inputs and outputs, and to generalize to new inputs that were not seen during training.

In some examples, the neural network 926 may also be one of a number of different types of neural networks or a combination thereof, such as a single-layer feed-forward network, a Multilayer Perceptron (MLP), an Artificial Neural Network (ANN), a Recurrent Neural Network (RNN), a Long Short-Term Memory Network (LSTM), a Bidirectional Neural Network, a symmetrically connected neural network, a Deep Belief Network (DBN), a Convolutional Neural Network (CNN), a Generative Adversarial Network (GAN), an Autoencoder Neural Network (AE), a Restricted Boltzmann Machine (RBM), a Hopfield Network, a Self-Organizing Map (SOM), a Radial Basis Function Network (RBFN), a Spiking Neural Network (SNN), a Liquid State Machine (LSM), an Echo State Network (ESN), a Neural Turing Machine (NTM), or a Transformer Network, merely for example.

In addition to the training phase 908, a validation phase may be performed evaluated on a separate dataset known as the validation dataset. The validation dataset is used to tune the hyperparameters of a model, such as the learning rate and the regularization parameter. The hyperparameters are adjusted to improve the performance of the model on the validation dataset.

The neural network 926 is iteratively trained by adjusting model parameters to minimize a specific loss function or maximize a certain objective. The system can continue to train the neural network 926 by adjusting parameters based on the output of the validation, refinement, or retraining block 812, and rerun the prediction 810 on new or already run training data. The system can employ optimization techniques for these adjustments such as gradient descent algorithms, momentum algorithms, Nesterov Accelerated Gradient (NAG) algorithm, and/or the like. The system can continue to iteratively train the neural network 926 even after deployment 814 of the neural network 926. The neural network 926 can be continuously trained as new data emerges, such as based on user creation or system-generated training data.

Once a model is fully trained and validated, in a testing phase, the model may be tested on a new dataset that the model has not seen before. The testing dataset is used to evaluate the performance of the model and to ensure that the model has not overfit the training data.

In prediction phase 910, the trained machine-learning program 902 uses the features 906 for analyzing query data 928 to generate inferences, outcomes, or predictions, as examples of a prediction/inference data 922. For example, during prediction phase 910, the trained machine-learning program 902 is used to generate an output. Query data 928 is provided as an input to the trained machine-learning program 902, and the trained machine-learning program 902 generates the prediction/inference data 922 as output, responsive to receipt of the query data 928. Query data can include a prompt, such as a user entering a textual question or speaking a question audibly. In some cases, the system generates the query based on an interaction function occurring in the system, such as a user interacting with a virtual object, a user sending another user a question in a chat window, or an object detected in a camera feed.

In some examples the trained machine-learning program 902 may be a generative AI model. Generative AI is a term that may refer to any type of artificial intelligence that can create new content from training data 904. For example, generative AI can produce text, images, video, audio, code or synthetic data that are similar to the original data but not identical.

Some of the techniques that may be used in generative AI are:

Convolutional Neural Networks (CNNs): CNNs are commonly used for image recognition and computer vision tasks. They are designed to extract features from images by using filters or kernels that scan the input image and highlight important patterns. CNNs may be used in applications such as object detection, facial recognition, and autonomous driving.

Recurrent Neural Networks (RNNs): RNNs are designed for processing sequential data, such as speech, text, and time series data. They have feedback loops that allow them to capture temporal dependencies and remember past inputs. RNNs may be used in applications such as speech recognition, machine translation, and sentiment analysis Generative adversarial networks (GANs): These are models that consist of two neural networks: a generator and a discriminator. The generator tries to create realistic content that can fool the discriminator, while the discriminator tries to distinguish between real and fake content. The two networks compete with each other and improve over time. GANs may be used in applications such as image synthesis, video prediction, and style transfer.

Variational autoencoders (VAEs): These are models that encode input data into a latent space (a compressed representation) and then decode it back into output data. The latent space can be manipulated to generate new variations of the output data. They may use self-attention mechanisms to process input data, allowing them to handle long sequences of text and capture complex dependencies.

Transformer models: These are models that use attention mechanisms to learn the relationships between different parts of input data (such as words or pixels) and generate output data based on these relationships. Transformer models can handle sequential data such as text or speech as well as non-sequential data such as images or code.

In generative AI examples, the prediction/inference data 922 that is output include trend assessment and predictions, translations, summaries, image or video recognition and categorization, natural language processing, face recognition, user sentiment assessments, advertisement targeting and optimization, voice recognition, or media content generation, recommendation, and personalization.

System Architecture for Applying Artificial Intelligence Using Intelligence Augmentation The embodiments described herein outlines a groundbreaking approach that combines artificial intelligence (AI) with intelligence augmentation (IA) in healthcare decision-making. Rather than solely AI controlling processes, some embodiments emphasize the clinician's expertise, with AI serving as a powerful tool to enhance decision-making and improve patient outcomes. The embodiments introduce a personalized recommendation system tailored to individual clinician preferences and patient characteristics, accessible across various platforms and designed for ease of use.

At its core, the system leverages contextual data from medical documents, clinical guidelines, and Clinical Quality Language (CQL) code. This data serves as training material for AI algorithms, enabling the development of advanced decision support tools that assist clinicians in adhering to guidelines and making informed decisions. The system's orchestration involves vector databases for efficient data analysis, large language models for domain-specific knowledge, and retrieval-augmented generation (RAG) techniques to enhance text generation and decision support.

The user interface is designed for simplicity and customization, offering low-code interfaces and command-line options to accommodate different user preferences and workflows. Validation and performance evaluation mechanisms ensure the accuracy and effectiveness of decision support artifacts, while real-time version control maintains up-to-date medical knowledge guidelines. Overall, this technology represents a significant leap forward in personalized decision support, empowering clinicians to deliver better care and optimize outcomes for their patients.

Figure 10:
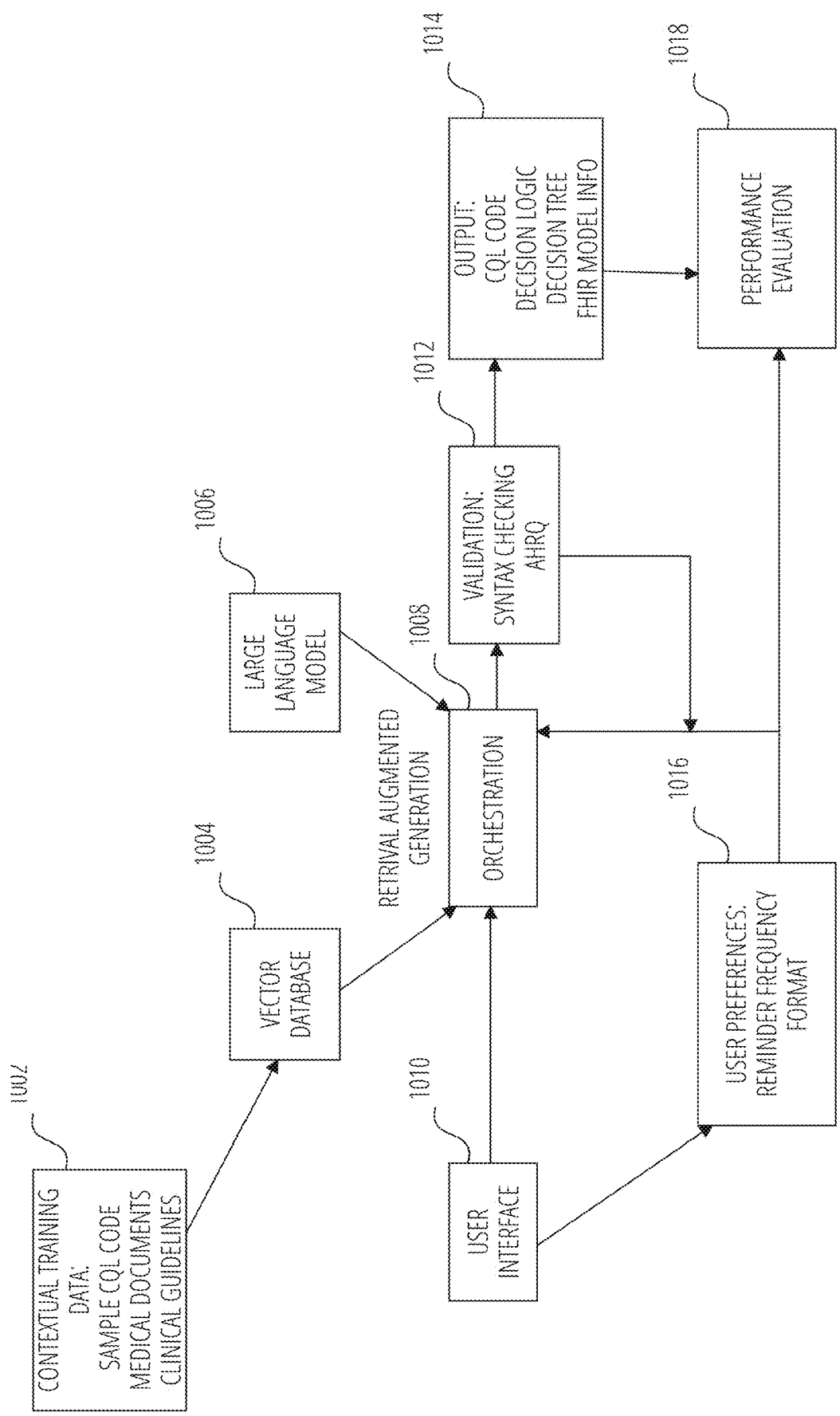
FIG. 10 illustrates a system architecture for applying artificial intelligence using intelligence augmentation, according to some examples.

FIG. 10 illustrates a system architecture for applying artificial intelligence using intelligence augmentation, according to some examples. The system architecture includes contextual training data 1002, a vector database 1004, a large language model 1006, orchestration module 1008, a user interface 1010, a validation module 1012, output 1014, user preferences 1016, and performance evaluation 1018.

Contextual training data includes specific information and elements extracted from medical documents, clinical guidelines, and Clinical Quality Language (CQL) code that are used to train artificial intelligence (AI) algorithms in the healthcare domain. This data plays a crucial role in teaching AI systems to understand and analyze the context of clinical decision-making, enabling them to provide relevant and accurate recommendations and decision support to clinicians.

Medical documents include patient records, medical histories, diagnostic reports, treatment plans, and other healthcare-related documents. Contextual training data from medical documents can encompass a wide range of information, such as patient demographics, symptoms, medical conditions, medications, lab results, imaging studies, procedures, and outcomes. AI algorithms learn from this data to recognize patterns, correlations, and trends within patient data, aiding clinicians in diagnosing conditions, planning treatments, and monitoring patient progress.

Clinical guidelines include evidence-based recommendations developed by healthcare organizations and expert panels to guide clinical practice and decision-making. Contextual training data from clinical guidelines includes recommendations for diagnosis, treatment protocols, medication dosages, preventive care measures, and follow-up procedures. AI algorithms learn from these guidelines to understand best practices, standard protocols, and evidence-based approaches in various medical scenarios. This knowledge helps AI systems provide decision support that aligns with established clinical guidelines, improving adherence to standards of care and patient outcomes.

CQL is a high-level, domain-specific language used in healthcare for defining and expressing clinical logic, quality measures, and decision support rules. Contextual training data from CQL code includes rules, logic statements, data elements, conditions, and criteria used in clinical decision-making algorithms. AI algorithms learn from this code to interpret and apply clinical logic, generate decision support recommendations, and assist clinicians in making informed decisions based on established rules and criteria.

In summary, contextual training data in healthcare encompasses a broad spectrum of information extracted from medical documents, clinical guidelines, and CQL code. This data serves as the foundation for training AI algorithms to understand clinical context, provide decision support, and improve healthcare outcomes by aligning with established standards, guidelines, and best practices.

A vector database includes a type of database specifically designed to store and manage vectors or high-dimensional data efficiently. Unlike traditional relational databases that store structured data in tables with rows and columns, a vector database is optimized for handling data represented as vectors, which are numerical arrays or sequences of values often used in machine learning and data analysis.

A vector database is designed to store vectors as primary data elements. Vectors can represent various types of data, such as embeddings of text, images, audio, or numerical features extracted from datasets. For example, in natural language processing (NLP), word embeddings or document embeddings can be stored as vectors in a vector database.

Vector databases use specialized indexing techniques to efficiently store and retrieve vectors based on their similarity or distance metrics. This allows for fast retrieval of similar vectors or nearest neighbors, which is crucial for tasks like similarity search, recommendation systems, and clustering.

Vector databases are designed to scale horizontally, meaning they can handle large volumes of vector data by distributing the workload across multiple nodes or servers. This scalability is essential for handling big data and real-time applications where the amount of vector data can grow rapidly.

Vector databases provide built-in support for vector operations and computations, such as cosine similarity, Euclidean distance, dot product, and vector transformations. These operations are fundamental for performing tasks like similarity search, clustering, and dimensionality reduction.

The system uses vector databases in conjunction with AI and machine learning workflows. The databases can store embeddings generated by machine learning models and serve as a data source for training and inference. AI applications, such as recommendation systems, image search, and anomaly detection, benefit from the efficient storage and retrieval of vector data.

The output of the contextual training data, which includes information extracted from medical documents, clinical guidelines, and Clinical Quality Language (CQL) code, can be transformed into vector representations before being fed into the vector database. This transformation process involves techniques like word embeddings for text data or feature extraction methods for structured data. These vector representations capture the semantic relationships, patterns, and contextual information present in the training data, allowing for efficient storage, indexing, and retrieval in the vector database. Once in the vector database, these representations enable tasks such as similarity search, recommendation systems, and clustering, enhancing the capabilities of AI-driven applications in healthcare decision-making.

A large language model (LLM) is a type of artificial intelligence model that is specifically designed to understand and generate human-like text. Unlike traditional machine learning models that focus on specific tasks (like image recognition or language translation), large language models are trained on vast amounts of text data to develop a deep understanding of language structure, semantics, and context. These models are capable of generating coherent and contextually relevant text, answering questions, completing sentences, and even engaging in conversations.

The large language model (LLM) applies natural language understanding (NLU) and natural language generation (NLG). The LLMs can comprehend complex language structures, infer meanings from context, and generate human-like responses. For example, LLMs can summarize text, answer questions based on passages, translate languages, and generate creative content like stories or poems.

The orchestration module plays a critical role in coordinating and managing the interactions between various components of the system, ensuring seamless workflow and optimal performance. The orchestration module integrates different components such as vector databases, large language models (LLMs), retrieval-augmented generation (RAG) techniques, user interfaces, and validation mechanisms. The orchestration module acts as a central hub that connects these components, allowing for data flow, communication, and collaboration between them.

One of the key tasks of the orchestration module is data processing and transformation. The orchestration module handles the transformation of contextual training data into vector representations suitable for storage in the vector database. This involves preprocessing, feature extraction, and vectorization techniques to convert raw data into structured and usable formats for AI algorithms.

The orchestration module oversees the execution of various tasks within the system. For example, the orchestration module coordinates the retrieval of relevant information from the vector database using similarity search or recommendation systems based on user queries or input data. The orchestration module also manages the generation of contextually relevant responses using LLMs and RAG techniques for decision support and recommendation generation.

Another important function of the orchestration module is workflow optimization. The orchestration module optimizes the sequence of operations, task distribution, and resource allocation to ensure efficient processing and performance. This includes prioritizing tasks, managing computational resources, and optimizing data pipelines for speed and accuracy.

The orchestration module incorporates error handling mechanisms to detect and address issues that may arise during task execution or data processing. The orchestration module also facilitates feedback loops for continuous improvement, allowing the system to learn from errors, user interactions, and performance metrics to enhance overall functionality and reliability.

Overall, the orchestration module serves as the backbone of the system, orchestrating the complex interactions and operations required for effective AI-driven decision support in healthcare. The orchestration module enables seamless integration, data transformation, task coordination, workflow optimization, error handling, and scalability, contributing significantly to the system's functionality, efficiency, and reliability.

The user interface (UI) includes graphical or command-line interface through which clinicians and users interact with the system to access and utilize its functionalities for decision support and recommendation generation. The user interface is designed to be accessible and user-friendly, catering to clinicians and users with varying levels of technical expertise. The user interface employs intuitive design principles, clear navigation structures, and interactive elements to enhance usability and facilitate efficient interaction with the system. Accessibility features ensure that the UI is inclusive and accessible to users with disabilities.

The user interface allows users to input queries, parameters, preferences, and configurations related to decision support tasks. For example, clinicians can enter patient data, clinical guidelines, and criteria for decision-making into the UI. They can also configure settings such as reminder frequency, format preferences, alert thresholds, and decision support rules based on their workflow and preferences.

The user interface facilitates interactive communication and feedback loops between users and the system. The user interface allows users to interact with generated recommendations, modify parameters, explore alternative options, and provide feedback on the system's performance. This interactivity promotes user engagement, collaboration, and continuous improvement of decision support functionalities.

The user interface seamlessly integrates with clinicians' existing workflows, electronic health record (EHR) systems, and healthcare IT environments. The user interface allows for easy integration of decision support artifacts, CQL code, clinical guidelines, and patient data, streamlining the process of accessing and applying decision support within clinical practice.

The validation module includes a component of the system that is responsible for ensuring the correctness, effectiveness, and compliance of decision support artifacts, rules, logic, and content generated or processed by the system. The validation module assesses the correctness and effectiveness of decision support artifacts, including rules, logic, data elements, and recommendations. The validation module verifies that the artifacts align with clinical guidelines, best practices, and regulatory standards. For example, in healthcare, the validation module checks the adherence of decision support artifacts to evidence-based medicine, medical protocols, and quality measures.

The validation module performs syntax checking to verify the structure, format, and language used in decision support artifacts. The validation module ensures compliance with the standards, specifications, and requirements of the authoring tool or platform used to create the artifacts. This includes checking rule syntax, data element references, decision logic, and overall design to prevent errors, inconsistencies, or non-compliance issues.

Quality assurance is a key aspect of the validation module's role. The validation module evaluates the quality, accuracy, and reliability of decision support artifacts in providing relevant and actionable recommendations to users. The module conducts tests, simulations, and validations to measure the performance, robustness, and generalizability of decision support functionalities.

The validation module incorporates clinical validation processes to gather feedback from clinicians, domain experts, and end-users. The validation module collects input, reviews outcomes, and solicits feedback on the usability, relevance, and impact of decision support artifacts in real-world clinical scenarios. This feedback loop helps refine and improve decision support functionalities based on actual user experiences and insights.

The validation module ensures that decision support artifacts comply with industry standards, guidelines, and regulations governing healthcare practices, data privacy, and ethical considerations. The validation module checks for adherence to standards such as Fast Healthcare Interoperability Resources (FHIR), Clinical Quality Language (CQL), and other relevant frameworks to maintain interoperability and data integrity.

The validation module supports continuous improvement through iterative validation cycles. The validation module iteratively refines, updates, and validates decision support artifacts based on feedback, performance metrics, user requirements, and evolving clinical guidelines. This iterative approach ensures that decision support functionalities remain accurate, relevant, and effective over time.

The output includes the results, information, and artifacts generated by the system as a result of processing input data, executing decision support tasks, and applying machine learning algorithms. The output includes Clinical Query Language (CQL) code, which represents the structured queries, rules, logic, and decision-making criteria derived from the system's analysis and processing of contextual data, clinical guidelines, and user inputs. This CQL code can be used to query databases, retrieve relevant information, and generate decision support recommendations based on predefined criteria and rules.

Decision logic text is part of the output and includes of logical rules, conditions, and algorithms that define how clinical decisions are made based on certain inputs, parameters, and decision-making criteria. This text-based representation helps clinicians understand the reasoning behind decision support recommendations, allowing for transparency, interpretation, and validation of decision-making processes.

The output may include decision tree diagrams, which visually represent the decision-making process using a tree-like structure. Decision tree diagrams show nodes representing decision points, branches indicating possible outcomes or actions, and leaf nodes representing final decisions or recommendations. These diagrams enhance explainability, visualization, and understanding of decision support pathways for clinicians and users.

The output includes FHIR model info, which represents structured data based on FHIR resources. This structured data format ensures interoperability, standardization, and compatibility with healthcare IT systems, electronic health records (EHRs), and other health information exchange platforms. FHIR model info facilitates seamless integration and sharing of healthcare data and decision support artifacts across healthcare settings.

The output may also include version control information and updates related to decision support artifacts, CQL code, decision logic text, and decision tree diagrams. Version control tracks revisions, updates, and changes made to decision support guidelines, ensuring that the information is always up-to-date, accurate, and reflective of the latest evidence-based practices and clinical guidelines.

The user preferences includes configurable settings, choices, and personalized configurations that users, such as clinicians or healthcare providers, can define within the system to tailor their experience and interactions with the decision support functionalities. User preferences allow clinicians to customize decision support interventions based on their workflow, clinical practices, and patient-specific needs. For example, clinicians can specify preferences related to the types of recommendations they want to receive (e.g., treatment options, diagnostic suggestions), the frequency of reminders or alerts, and the format of decision support outputs (e.g., visual graphics, text summaries).

User preferences include settings related to reminder frequency, timing, and scheduling of decision support alerts or notifications. Clinicians can configure how often they receive reminders or updates, the preferred timing (e.g., during patient consultations, before critical decisions), and the urgency levels for different types of alerts.

User preferences allow clinicians to choose the format and presentation style of decision support information. This includes options such as visual graphics, interactive charts, textual summaries, decision trees, or annotated guidelines. Clinicians can select the format that best suits their preferences for information consumption and decision-making processes.

User preferences enable content customization and filtering based on specific criteria or criteria sets. Clinicians can define rules, triggers, and filters to prioritize certain types of information, exclude irrelevant data, or focus on specific patient populations, conditions, or clinical scenarios. This customization enhances the relevance and accuracy of decision support recommendations.

User preferences may include settings related to the integration of decision support artifacts from external sources or authoring tools. Clinicians can specify preferences for selecting guidelines, protocols, or decision rules from repositories, web sources, or de novo creation. They can also define how decision support information is presented, explained, and contextualized within the user interface.

User preferences facilitate feedback mechanisms and iterative improvement cycles. Clinicians can provide feedback on the relevance, usefulness, and effectiveness of decision support recommendations based on their preferences and experiences. This feedback loop allows for continuous refinement, optimization, and enhancement of decision support functionalities based on user input and insights.

Performance evaluation includes systematic assessment, analysis, and measurement of the system's performance, effectiveness, and impact on decision-making processes and healthcare outcomes. Performance evaluation includes quality assurance processes to ensure that decision support artifacts, recommendations, and outcomes meet established standards of accuracy, reliability, and effectiveness. Performance evaluation involves comparing system-generated outputs with expected or desired outcomes, clinical guidelines, best practices, and domain-specific criteria to assess accuracy and correctness.

Performance evaluation incorporates clinical validation processes that gather feedback from clinicians, domain experts, and end-users regarding the system's usability, relevance, and impact on decision-making. Performance evaluation collects input, reviews outcomes, and solicits feedback on the system's performance in real-world clinical scenarios. This feedback loop helps refine and improve decision support functionalities based on actual user experiences and insights.

Performance evaluation defines evaluation metrics and key performance indicators (KPIs) to measure the system's performance across various dimensions. These metrics may include accuracy rates, precision, recall, F1 score, sensitivity, specificity, false positive rates, false negative rates, and other relevant measures to quantify system performance, reliability, and predictive capabilities.

Performance evaluation assesses the system's robustness and generalizability across different datasets, patient populations, clinical scenarios, and healthcare settings. Performance evaluation examines how well the system performs under varying conditions, data distributions, and input variations to ensure consistent and reliable performance in diverse real-world contexts.

Performance evaluation evaluates the clinical utility and impact of decision support functionalities on healthcare outcomes, patient care, and clinical decision-making processes. It assesses whether the system contributes to improved patient outcomes, reduced errors, optimized workflows, and enhanced clinician decision-making efficiency.

Performance evaluation supports continuous improvement through iterative validation cycles. Performance evaluation iteratively refines, updates, and validates decision support functionalities based on feedback, performance metrics, user requirements, and evolving clinical guidelines. This iterative approach ensures that the system remains accurate, relevant, and effective over time and adapts to changing healthcare needs and challenges.

EXAMPLES

In view of the above-described implementations of subject matter this application discloses the following list of examples, wherein one feature of an example in isolation or more than one feature of an example, taken in combination and, optionally, in combination with one or more features of one or more further examples are further examples also falling within the disclosure of this application.

Example 1 is a system comprising: at least one processor; and at least one memory component storing instructions that, when executed by the at least one processor, cause the at least one processor to perform operations comprising: receiving a disease specific treatment algorithm corresponding to a disease of a patient from a first Electronic Health Record (EHR) system; processing data corresponding to the disease specific treatment algorithm using a Large Language Model (LLM), the LLM being trained to process disease specific treatment algorithms to generate Clinical Quality Language (CQL) models compatible for FHIR; receiving one or more CQL models from the LLM based on the processing of the data corresponding to the disease specific treatment algorithm; receiving an update to a patient record of the patient from the first EHR system; based on the update to the patient record and the one or more CQL models, triggering a Clinical Decision Support (CDS) hook to generate an alert; and causing transmission of the alert for a medical practitioner associated with the first EHR system.

In Example 2, the subject matter of Example 1 includes, wherein the disease specific treatment algorithm comprises a decision tree that applies information of a patient's EHR and outputs one or more treatment procedures for the patient.

In Example 3, the subject matter of Examples 1-2 includes, wherein the one or more CQL models include a decision tree that applies information of a patient's electronic health record and outputs one or more treatment procedures for the patient in a standardized form compatible with FHIR systems.

In Example 4, the subject matter of Examples 1-3 includes, wherein the LLM is trained to retrieve a patient's EHR and apply the patient's EHR to the one or more CQL models to generate one or more treatment procedures for the patient.

In Example 5, the subject matter of Example 4 includes, wherein the update of the patient records is applied to the one or more treatment procedures, wherein triggering the CDS hook comprises an indication of a failure for the one or more treatment procedures.

In Example 6, the subject matter of Examples 4-5 includes, wherein retrieving the patient's EHR comprises retrieving the patient's EHR from the first EHR system.

In Example 7, the subject matter of Examples 4-6 includes, wherein the first EHR system selects the disease specific treatment algorithm for the patient, wherein retrieving the patient's EHR comprises retrieving the patient's EHR from a second EHR system different than the first EHR system.

In Example 8, the subject matter of Examples 4-7 includes, wherein the patient's EHR comprises a digital version of a paper chart of an assessment by a medical practitioner of the patient.

In Example 9, the subject matter of Examples 4-8 includes, wherein the patient's EHR indicates a plurality of diseases, wherein the operations further comprise processing data associated with a plurality of disease specific treatment algorithms for individual diseases of the plurality of diseases using the LLM to generate the one or more treatments.

In Example 10, the subject matter of Examples 1-9 includes, wherein the operations further comprise retrieving a patient's EHR; and applying the patient's EHR to the one or more CQL models to generate one or more treatment procedures for the patient, wherein the update of the patient records is applied to the one or more treatment procedures.

In Example 11, the subject matter of Example 10 includes, wherein triggering the CDS hook comprises an indication of a failure for the one or more treatment procedures.

In Example 12, the subject matter of Examples 1-11 includes, wherein triggering the CDS hook is further based on an indication of a failure in the update to the patient record to prescribe a correct dosage of a medication.

In Example 13, the subject matter of Examples 1-12 includes, wherein triggering the CDS hook is further based on an indication of a failure in the update to the patient record to prescribe a medication at a particular time.

In Example 14, the subject matter of Examples 1-13 includes, wherein triggering the CDS hook is further based on an indication of a newly prescribed medication in the update to the patient record.

In Example 15, the subject matter of Examples 1-14 includes, wherein triggering the CDS hook is further based on an indication of a new patient record opened in the update to the patient record.

In Example 16, the subject matter of Examples 1-15 includes, wherein the alert comprises a user selectable interface element, wherein in response to a user selection of the user selectable interface element, the system initiates communication with a third party server associated with a pharmacy to create, update, modify, or cancel a medication request.

In Example 17, the subject matter of Examples 1-16 includes, wherein the operations further comprise: training the LLM by: identifying training disease specific treatment algorithms and corresponding expected training CQL models for the training disease specific treatment algorithms; applying the training disease specific treatment algorithms to the LLM to receive output CQL models; compare the output CQL models with the expected training CQL models to determine a loss parameter for the LLM; and update a characteristic of the LLM based on the loss parameter.

In Example 18, the subject matter of Examples 1-17 includes, wherein the operations further comprise: determining an update to the CQL model; and retraining the LLM using training CQL models that are based on the updated CQL model.

Example 19 is a method comprising: receiving a disease specific treatment algorithm corresponding to a disease of a patient from a first Electronic Health Record (EHR) system; processing data corresponding to the disease specific treatment algorithm using a Large Language Model (LLM), the LLM being trained to process disease specific treatment algorithms to generate Clinical Quality Language (CQL) models compatible for FHIR; receiving one or more CQL models from the LLM based on the processing of the data corresponding to the disease specific treatment algorithm; receiving an update to a patient record of the patient from the first EHR system; based on the update to the patient record and the one or more CQL models, triggering a Clinical Decision Support (CDS) hook to generate an alert; and causing transmission of the alert for a medical practitioner associated with the first EHR system.

Example 20 is a non-transitory computer-readable storage medium storing instructions that, when executed by at least one processor, cause the at least one processor to perform operations comprising: receiving a disease specific treatment algorithm corresponding to a disease of a patient from a first Electronic Health Record (EHR) system; processing data corresponding to the disease specific treatment algorithm using a Large Language Model (LLM), the LLM being trained to process disease specific treatment algorithms to generate Clinical Quality Language (CQL) models compatible for FHIR; receiving one or more CQL models from the LLM based on the processing of the data corresponding to the disease specific treatment algorithm; receiving an update to a patient record of the patient from the first EHR system; based on the update to the patient record and the one or more CQL models, triggering a Clinical Decision Support (CDS) hook to generate an alert; and causing transmission of the alert for a medical practitioner associated with the first EHR system.

Example 21 is at least one machine-readable medium including instructions that, when executed by processing circuitry, cause the processing circuitry to perform operations to implement any of Examples 1-20.

Example 22 is an apparatus comprising means to implement any of Examples 1-20.

Example 23 is a system to implement any of Examples 1-20. Example 24 is a method to implement any of Examples 1-20.

CONCLUSION

As used in this disclosure, phrases of the form "at least one of an A, a B, or a C," "at least one of A, B, or C," "at least one of A, B, and C," and the like, should be interpreted to select at least one from the group that comprises "A, B, and C." Unless explicitly stated otherwise in connection with a particular instance in this disclosure, this manner of phrasing does not mean "at least one of A, at least one of B, and at least one of C." As used in this disclosure, the example "at least one of an A, a B, or a C," would cover any of the following selections: {A}, {B}, {C}, {A, B}, {A, C}, {B, C}, and {A, B, C}.

Unless the context clearly requires otherwise, throughout the description and the claims, the words "comprise," "comprising," and the like are to be construed in an inclusive sense, as opposed to an exclusive or exhaustive sense, i.e., in the sense of "including, but not limited to." As used herein, the terms "connected," "coupled," or any variant thereof means any connection or coupling, either direct or indirect, between two or more elements; the coupling or connection between the elements can be physical, logical, or a combination thereof. Additionally, the words "herein," "above," "below," and words of similar import, when used in this application, refer to this application as a whole and not to any particular portions of this application. Where the context permits, words using the singular or plural number may also include the plural or singular number respectively. The word "or" in reference to a list of two or more items, covers all of the following interpretations of the word: any one of the items in the list, all of the items in the list, and any combination of the items in the list. Likewise, the term "and/or" in reference to a list of two or more items, covers all of the following interpretations of the word: any one of the items in the list, all of the items in the list, and any combination of the items in the list.

Although some examples, e.g., those depicted in the drawings, include a particular sequence of operations, the sequence may be altered without departing from the scope of the present disclosure. For example, some of the operations depicted may be performed in parallel or in a different sequence that does not materially affect the functions as described in the examples. In other examples, different components of an example device or system that implements an example method may perform functions at substantially the same time or in a specific sequence.

The various features, steps, and processes described herein may be used independently of one another, or may be combined in various ways. All possible combinations and subcombinations are intended to fall within the scope of this disclosure. In addition, certain method or process blocks may be omitted in some implementations.

What is claimed is:

1. A system comprising:
   at least one processor; and
   at least one memory component storing instructions that, when executed by the at least one processor, cause the at least one processor to perform operations comprising:
   receiving a disease specific treatment algorithm corresponding to a disease of a patient from a first Electronic Health Record (EHR) system, the disease specific treatment algorithm including a decision tree that includes guidelines for treating a specific disease;
   processing data corresponding to the disease specific treatment algorithm by inputting the data into a Large Language Model (LLM), the LLM being trained to process disease specific treatment algorithms to generate Clinical Quality Language (CQL) models compatible for Fast Healthcare Interoperability Resources (FHIR) and configured to trigger Clinical Decision Support (CDS) hooks;
   receiving one or more first COL models from the LLM based on the processing of the data corresponding to the disease specific treatment algorithm, the one or more first COL models include at least a first CDS hook;
   receiving an update to a patient record of the patient from the first EHR system;
   generating an updated disease specific treatment algorithm based on the update;
   inputting the updated disease specific treatment algorithms to the LLM to receive one or more second CQL models from the LLM;

executing the one or more second CQL models triggering at least a second CDS hook to generate an alert; and causing transmission of the alert for a medical practitioner associated with the first EHR system.

2. The system of claim 1, wherein the disease specific treatment algorithm comprises a decision tree that applies information of a patient's EHR and outputs one or more treatment procedures for the patient.

3. The system of claim 1, wherein the one or more second CQL models include a decision tree that applies information of a patient's electronic health record and outputs one or more treatment procedures for the patient in a standardized form compatible with FHIR systems.

4. The system of claim 1, wherein the LLM is trained to retrieve a patient's EHR and apply the patient's EHR to the one or more second COL models to generate one or more treatment procedures for the patient.

5. The system of claim 4, wherein the update of the patient records is applied to the one or more treatment procedures, wherein triggering at least the second CDS hook comprises an indication of a failure for the one or more treatment procedures.

6. The system of claim 4, wherein retrieving the patient's EHR comprises retrieving the patient's EHR from the first EHR system.

7. The system of claim 4, wherein the first EHR system selects the disease specific treatment algorithm for the patient, wherein retrieving the patient's EHR comprises retrieving the patient's EHR from a second EHR system different than the first EHR system.

8. The system of claim 4, wherein the patient's EHR comprises a digital version of a paper chart of an assessment by a medical practitioner of the patient.

9. The system of claim 4, wherein the patient's EHR indicates a plurality of diseases, wherein the operations further comprise processing data associated with a plurality of disease specific treatment algorithms for individual diseases of the plurality of diseases using the LLM to generate the one or more treatments.

10. The system of claim 1, wherein the operations further comprise:

retrieving a patient's EHR; and applying the patient's EHR to the one or more second CQL models to generate one or more treatment procedures for the patient, wherein the update of the patient records is applied to the one or more treatment procedures.

11. The system of claim 10, wherein triggering at least the second CDS hook comprises an indication of a failure for the one or more treatment procedures.

12. The system of claim 1, wherein triggering at least the second CDS hook is further based on an indication of a failure in the update to the patient record to prescribe a correct dosage of a medication.

13. The system of claim 1, wherein triggering at least the second CDS hook is further based on an indication of a failure in the update to the patient record to prescribe a medication at a particular time.

14. The system of claim 1, wherein triggering at least the second CDS hook is further based on an indication of a newly prescribed medication in the update to the patient record.

15. The system of claim 1, wherein triggering at least the second CDS hook is further based on an indication of a new patient record opened in the update to the patient record.

16. The system of claim 1, wherein the alert comprises a user selectable interface element, wherein in response to a user selection of the user selectable interface element, the system initiates communication with a third party server associated with a pharmacy to create, update, modify, or cancel a medication request.

17. The system of claim 1, wherein the operations further comprise:

training the LLM by:

identifying training disease specific treatment algorithms and corresponding expected training CQL models for the training disease specific treatment algorithms;

applying the training disease specific treatment algorithms to the LLM to receive output COL models;

compare the output CQL models with the expected training CQL models to determine a loss parameter for the LLM; and update a characteristic of the LLM based on the loss parameter.

18. The system of claim 1, wherein the operations further comprise:

determining an update to the COL model; and retraining the LLM using training CQL models that are based on the updated COL model.

19. A method comprising:

receiving a disease specific treatment algorithm corresponding to a disease of a patient from a first Electronic Health Record (EHR) system, the disease specific treatment algorithm including a decision tree that includes guidelines for treating a specific disease;

processing data corresponding to the disease specific treatment algorithm by inputting the data into a Large Language Model (LLM), the LLM being trained to process disease specific treatment algorithms to generate Clinical Quality Language (CQL) models compatible for Fast Healthcare Interoperability Resources (FHIR) and configured to trigger Clinical Decision Support (CDS) hooks;

receiving one or more first COL models from the LLM based on the processing of the data corresponding to the disease specific treatment algorithm, the one or more first COL models include at least a first CDS hook;

receiving an update to a patient record of the patient from the first EHR system;

generating an updated disease specific treatment algorithm based on the update;

inputting the updated disease specific treatment algorithm to the LLM to receive one or more second CQL models from the LLM;

executing the one or more second CQL models triggering at least a second CDS hook to generate an alert; and causing transmission of the alert for a medical practitioner associated with the first EHR system.

20. A non-transitory computer-readable storage medium storing instructions that, when executed by at least one processor, cause the at least one processor to perform operations comprising:

receiving a disease specific treatment algorithm corresponding to a disease of a patient from a first Electronic Health Record (EHR) system, the disease specific treatment algorithm including a decision tree that includes guidelines for treating a specific disease;

processing data corresponding to the disease specific treatment algorithm by inputting the data into a Large Language Model (LLM), the LLM being trained to process disease specific treatment algorithms to generate Clinical Quality Language (CQL) models compatible for Fast Healthcare Interoperability Resources (FHIR) and configured to trigger Clinical Decision Support (CDS) hooks;

receiving one or more first CQL models from the LLM based on the processing of the data corresponding to the disease specific treatment algorithm, the one or more first CQL models include at least a first CDS hook;

receiving an update to a patient record of the patient from the first EHR system;

generating an updated disease specific treatment algorithm based on the update;

inputting the updated disease specific treatment algorithms to the LLM to receive one or more second CQL models from the LLM;

executing the one or more second CQL models triggering at least a second CDS hook to generate an alert; and causing transmission of the alert for a medical practitioner associated with the first EHR system.

* * * * *

UNITED STATES PATENT AND TRADEMARK OFFICE
CERTIFICATE OF CORRECTION

PATENT NO. : 12,431,226 B2  
APPLICATION NO. : 18/673079  
DATED : September 30, 2025  
INVENTOR(S) : Fredric A. Santiago Page 1 of 1

It is certified that error appears in the above-identified patent and that said Letters Patent is hereby corrected as shown below:

In the Claims

In Column 36, Line 56, in Claim 1, delete "COL" and insert --CQL-- therefor

In Column 36, Line 59, in Claim 1, delete "COL" and insert --CQL-- therefor

In Column 37, Line 16, in Claim 4, delete "COL" and insert --CQL-- therefor

In Column 37, Line 41, in Claim 10, delete "comprise;" and insert --comprise:-- therefor In Column 38, Line 12, in Claim 17, delete "COL" and insert --CQL-- therefor In Column 38, Line 21, in Claim 18, delete "COL" and insert --CQL-- therefor In Column 38, Line 23, in Claim 18, delete "COL" and insert --CQL-- therefor In Column 38, Line 38, in Claim 19, delete "COL" and insert --CQL-- therefor In Column 38, Line 41, in Claim 19, delete "COL" and insert --CQL-- therefor In Column 39, Line 14, in Claim 20, after "algorithm", delete "s"

Signed and Sealed this  
Eleventh Day of November, 2025

John A. Squires  
*Director of the United States Patent and Trademark Office*